US008754124B2

(12) United States Patent
Ahn et al.

(10) Patent No.: US 8,754,124 B2
(45) Date of Patent: Jun. 17, 2014

(54) OLIGO-BENZAMIDE COMPOUNDS AND THEIR USE IN TREATING CANCERS

(71) Applicant: The Board of Regents of the University of Texas System, Austin, TX (US)

(72) Inventors: Jung-Mo Ahn, Plano, TX (US); Ganesh Raj, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/683,932

(22) Filed: Nov. 21, 2012

(65) Prior Publication Data

US 2013/0150442 A1 Jun. 13, 2013

Related U.S. Application Data

(60) Provisional application No. 61/563,437, filed on Nov. 23, 2011, provisional application No. 61/664,372, filed on Jun. 26, 2012.

(51) Int. Cl.
*A61K 31/24* (2006.01)
*C07C 233/00* (2006.01)

(52) U.S. Cl.
USPC ........... 514/537; 514/616; 514/535; 564/153; 564/158; 560/21

(58) Field of Classification Search
USPC ................. 514/537, 616, 535; 564/153, 158; 560/21
See application file for complete search history.

(56) References Cited

U.S. PATENT DOCUMENTS

| | | | | |
|---|---|---|---|---|
| 5,212,203 | A | 5/1993 | Shroot et al. | 514/617 |
| 5,929,114 | A | 7/1999 | Domagala et al. | 514/562 |
| 7,217,720 | B2 | 5/2007 | Meissner et al. | 514/284 |
| 7,816,324 | B2 * | 10/2010 | Ahn et al. | 514/7.2 |
| 7,906,624 | B2 | 3/2011 | Green et al. | 530/387.3 |
| 8,236,983 | B2 * | 8/2012 | Ahn | 562/453 |
| 2005/0261346 | A1 | 11/2005 | Zhu et al. | 514/332 |
| 2007/0248535 | A1 | 10/2007 | Buttyan et al. | 424/1.49 |
| 2009/0012141 | A1 | 1/2009 | Ahn | 514/400 |
| 2009/0275519 | A1 | 11/2009 | Nash et al. | 514/1.1 |
| 2010/0069333 | A1 | 3/2010 | Kahn | 514/80 |
| 2010/0125055 | A1 | 5/2010 | Kufe et al. | 514/13 |
| 2010/0178324 | A1 * | 7/2010 | Ahn | 424/450 |
| 2010/0317570 | A1 | 12/2010 | Ahn et al. | 514/4.8 |
| 2013/0011465 | A1 | 1/2013 | Ahn | 424/450 |
| 2013/0184345 | A1 | 7/2013 | Ahn et al. | 514/535 |

FOREIGN PATENT DOCUMENTS

| | | |
|---|---|---|
| WO | WO 2008/112938 | 9/2008 |
| WO | WO 2008/112939 | 9/2008 |
| WO | WO 2008/112941 | 9/2008 |
| WO | WO 2010/088498 | 8/2010 |
| WO | WO 2011/050353 | 4/2011 |
| WO | WO 2011/150360 | 12/2011 |

OTHER PUBLICATIONS

Ahn et al. CAS: 147: 72511, 2007.*
Han et al. CAS: 154: 401514, 2010.*
Plante et al. CAS: 151: 439821, 2009.*
Ahn's CAS: 149: 378403, 2008.*
Izmail'skii et al. CAS: 31: 30601, 1937.*
Adams et al., "Life-or-death decisions by the Bcl-2 protein family," *Trends Biochem. Sci*, 26:61-66, 2001.
Ahn et al., "A new approach to search the bioactive conformation of glucagon: positional cyclization scanning," *J. Med. Chem.*, 44:3109-3116, 2001.
Ahn et al., "Development of potent truncated glucagon antagonists," *J. Med. Chem.*, 44:1372-1379, 2001.
Ahn et al., "Facile synthesis of benzamides to mimic an α-helix," *Tetrahedron Letters*, 48:3543-3547, 2007.
Ahn et al., "Peptidomimetics and peptide backbone modifications," *Mini-Reviews in Medicinal Chemistry*, 2:463-473, 2002.
Bulotta et al., "A cultured pancreatic ductal cells undergo cell cycle re-distribution and beta-cell-like differentiation in response to glucagon-like peptide-1," *J. Mol. Endocrinol.*, 29:347-360, 2002.
Burgess et al., "Solid-phase syntheses of β-turn analogues to mimic or disrupt protein-protein interactions," *Acc. Chem. Res.*, 24:826-835, 2001.
Cavaghan et al., "Interactions between insulin resistance and insulin secretion in the development of glucose intolerance," *J. Clin. Invest.*, 106:329-333, 2000.
Chang et al., "Substituted imidazoles as glucagon receptor antagonists," *Bioorg. Med. Chem. Lett.*, 11:2549-2553, 2001.
Chapuis et al., "Shorter puromycin analog synthesis by means of an efficient Staudinger-Vilarrasa coupling," *Tetrahedron*, 62:12108-12115, 2006.
Chen et al., "A nonpeptidic agonist of glucagon-like peptide 1 receptors with efficacy in diabetic db/db mice," *Proc. Natl. Acad. Sci. USA*, 104:943-948, 2007.
Chittenden et al., "A conserved domain in Bak, distinct from BH1 and BH2, mediates cell death and protein binding functions," *EMBO J.*, 14:5589-5596, 1995.
Cochran, "Antagonists of protein-protein interactions," *Chem. Biol.*, 7:R85-R94, 2000.
Database CAPLUS on STN, Acc. No. 2007:1424768, Plante et al., *Organic & Biomolecular Chemistry*, 6(1):138-146, 2008. (Abstract).
Defronzo et al., "Effects of exenatide (exendin-4) on glycemic control and weight over 30 weeks in metformin-treated patients with type 2 diabetes," *Diabetes Care*, 28:1092-1100, 2005.

(Continued)

*Primary Examiner* — Rei-tsang Shiao
(74) *Attorney, Agent, or Firm* — Parker Highlander, PLLC

(57) ABSTRACT

The present invention includes bis- and tris-benzamide compounds that block AR signaling and have activity against prostate cancer. Uses for these compounds, and pharmaceutical compositions containing the same, also are provided.

34 Claims, 12 Drawing Sheets

(56) References Cited

OTHER PUBLICATIONS

Dehm, et al., "Selective role of an NH2-terminal WxxLF motif for aberrant androgen receptor activation in androgen depletion independent prostate cancer cells," *Cancer Res.*, 67:10067-77, 2007.

Drucker et al., "The incretin system: glucagon-like peptide-1 receptor agonists and dipeptidyl peptidase-4 inhibitors in type 2 diabetes," *Lancet*, 368:1696-1705, 2006.

Edwards et al., "Exendin-4 reduces fasting and postprandial glucose and decreases energy intake in healthy volunteers," *Am. J. Physiol. Endocrinol. Metab.*, 281:E155-E161, 2001.

Egan et al., "GLP-1 receptor antagonists are growth and differentiation factors for pancreatic islet beta cells," *Diabetes/Metab. Res. Rev.*, 19:115-123, 2003.

Elbronds et al., "Pharmacokinetics, pharmacodynamics, safety, and tolerability of a single-dose of NN2211, a long-acting glucagon-like peptide 1 derivative, in healthy male subjects," *Diabetes Care*, 25:1398-1404, 2002.

Ernst et al., "Design and application of an α-helixmimetic scaffold based on an oligoamide-foldamer strategy: antagonism of the Bak BH3/Bc1-xL. complex," *Angew. Chem. Int. Ed.*, 42:535-539, 2003.

Gunther, et al., "Alternative inhibition of androgen receptor signaling: peptidomimetic pyrimidines as direct androgen receptor/coactivator disruptors," *ACS Chem. Biol.*, 4:435-40, 2009.

Hoare et al., "Mechanisms of peptide and nonpepetide ligand binding to class B G-proteincoupled receptors," *Drug Discovery Today*, 10:417-427, 2005.

Hruby et al., "Design in topographical space of peptide and peptidomimetic ligands that affect behavior. A chemist's glimpse at the mind—body problem," *Acc. Chem. Res.*, 34(5):389-397, 2001.

Jacoby et al., "Biphenyls as potential mimetics of protein α-helix," *Bioorg. Med. Chem. Lett.*, 12:891-893, 2002.

Knudsen et al., "Glucagon-like peptide-1: the basis of a new class of treatment for type 2 diabetes," *J. Med. Chem.*, 47:4128-4134, 2004.

Knudsen et al., "Small-molecule agonists for the glucagon-like peptide 1 receptor," *Proc. Natl. Acad. Sci. U.S.A.*, 104:937-942, 2007.

Kolterman et al., "Synehetic exendin-4 (exenatide) significantly reduces postprandial and fasting plasma glucose in subjects with type 2 diabetes," *J. Clin. Endocrinol. Metab.*, 88:3082-3089, 2003.

Konig et al., "Solid-phase synthesis of oligo(p-benzamide) foldamers," *Organic Letters*, 8:1819-1822, 2006.

Konig et al., "Supramolecular PEG-co-Olige(p-benzamide)s prepared on a peptide synthezier," *J. Am. Chem. Soc.*, 129:704-708, 2007. Published on Web Dec. 23, 2006.

Kussie et al., "Structure of the MDM2 oncoprotein bound to the p53 tumor suppressor transactivation domain," *Science*, 274:948-953, 1996.

Kutzki et al., "Development of a potent Bcl-xL antagonist based on α-helix mimicry," *J. Am. Chem. Soc.*, 124:11838-11839, 2002.

Ling et al., "Identification of alkylidene hydrazides as glucagon receptor antagonists," *J. Med. Chem.*, 44:3141-3149, 2001.

Madsen et al., "Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide," *J. Med. Chem.*, 45:5755-5775, 2002.

Mahato et al., "Emerging trends in oral delivery of peptide and protein drugs," *Critical Reviews in Therapeutic Drug Carrier Systems*, 20:153-214, 2003.

Marshall, et al., "A hierarchical approach to peptidomimetic design," *Tetrahedron*, 49:3547-3558, 1993.

Matias, et al., "Structural evidence for ligand specificity in the binding domain of the human androgen receptor" *J. Bio. Chem.*, 275:26164-71, 2000.

Murphy, "Nonpeptidic glucagon-like peptide 1 receptor agonists: A magic bullet for diabetes," *Proc. Natl. Acad. Sci. U.S.A.*, 104:689-690, 2007.

Neidigh et al., "Exendin-4 and glucagon-likepeptide-1: NMR structural comparisons in the solution and micelle-associated states," *Biochemistry*, 40:13188-13200, 2001.

Office Action issued in U.S. Appl. No. 12/048,197, mailed Jan. 14, 2013.

Office Communication issued in U.S. Appl. No. 12/353,173, dated Jan. 11, 2012.

Office Communication issued in U.S. Appl. No. 12/353,173, dated Jun. 23, 2011.

Office Communication issued in U.S. Appl. No. 12/353,173, dated Mar. 24, 2011.

Office Communication issued in U.S. Appl. No. 12/048,197, dated May 9, 2012.

Office Communication issued in U.S. Appl. No. 12/048,197, dated Mar. 23, 2012.

Office Communication issued in U.S. Appl. No. 12/048,197, dated Feb. 23, 2012.

Office Communication issued in U.S. Appl. No. 12/048,197, dated Jul. 6, 2011.

Office Communication issued in U.S. Appl. No. 12/048,197, dated Sep. 22, 2010.

Office Communication issued in U.S. Appl. No. 12/048,197, dated Jul. 12, 2010.

Oguri et al., "Design and synthesis of a trans-fused polycyclic ether skeleton as an a-helix mimetic scaffold," *Tetrahedron Lett.*, 46:2179-2183, 2005.

Orner et al., "Towards proteomimetics: Terphenyl derivatives as structural and functional mimics of extended regions of an α-helix," *J. Am. Chem. Soc.*, 123:5382-5383, 2001.

PCT International Search Report and Written Opinion, issued in Application No. PCT/US2012/066212, dated Mar. 1, 2013.

PCT International Search Report and Written Opinion, issued in Application No. PCT/US2012/066228, dated Feb. 8, 2013.

PCT International Search Report and Written Opinion, issued in Application No. PCT/US2011/038395, dated Sep. 13, 2011.

PCT International Search Report and Written Opinion issued in International Application No. PCT/US2010/020898, dated Aug. 20, 2010.

PCT International Search Report and Written Opinion issued in International Application No. PCT/US2008/056920, dated Aug. 1, 2008.

PCT International Search Report and Written Opinion issued in International Application No. PCT/US2008/056918, dated Sep. 10, 2008.

Peczuh et al., "Peptide and protein recognition by designed molecules," *Chem. Rev..*, 100:2479-2494, 2000.

Perry et al., "The glucagon-like peptides: a double-edged therapeutic sword," *Trends Pharmacol. Sci.*, 24:377-383, 2003.

Plante et al., "Synthesis of functionalised aromatic oligamide rods," *Organic & Biomolecular Chemistry*, 6:138-146, 2008.

Rickard et al., "Intermittend treatment with parathyroid hormone (PTH) as well as a non-petide small molecule agonist of the PTH1 receptor inhibits adipocyte differentiation in human bone marrow stromal cells," *Bone*, 39:1361-1372, 2006.

Runge et al., Different domains of the glucagon and glucagon-like peptide-1 receptors provide the critical determinants of ligand selectivity, *Br. J. Pharmacol.*, 138:787-794, 2003.

Saragoi et al., "Synthetic α-helix mimetics as agonists and antagonists of islet amyloid polypeptide aggregation," *Angewandte Chemie*, 49:736-739, 2010.

Sattler et al., "Structure of Bcl-xL-Bak peptide complex: Recognition between regulators of apoptosis," *Science*, 275:983-986, 1997.

Souers et al., "β-Turn mimetic library synthesis: scaffolds and applications," *Tetrahedron*, 57:7431-7448, 2001.

Stoffers et al., "Insulinotropics glucagon-like peptide 1 agonists stimulate expression of homeodomain protein IDX-1 and increase islet size in mouse pancreas," *Diabetes*, 49:741-749, 2000.

Tanatani et al., "Helical structures of N-alkylated poly(p-benzamide)s," *J. Am. Chem. Soc.*, 127:8553-8561, 2005.

Tibaduiza et al., "A small molecule ligand of the glucagon-like peptide 1 receptor targets its amino-terminal hormone binding domain," *J. Biol. Chem.*, 276:37787-37793, 2001.

Toft-Nielsen et al., "Determinants of the effectiveness of glucagon-like peptide-1 in type 2 diabetes," *J. Clin. Endocrinol. Metab.*, 86:3853-3860, 2001.

(56) References Cited

OTHER PUBLICATIONS

Vilsboll et al., "No reactive hypoglycaemia in type 2 diabetic patients after subcutaneous administration of GLP-1 and intravenous glucose," *Diabetic Med.*, 18:144-149, 2001.

Walensky et al., "Activation of apoptosis in vivo by a hydrocarbon-stapled BH3 helix," *Science*, 305:1466-1470, 2004.

Yin et al., "Terephthalamide derivatives as mimetics of helical peptides: Disruption of the Bcl-xL/Bak interaction," *J. Am. Chem. Soc.*, 127:5463-5468, 2005.

Yin et al., "Terphenyl-based Bak BH3 α-helical proteomimetics as low-molecular-weight antagonists of Bcl-xL," *J. Am. Chem. Soc.*, 127:10191-10196, 2005.

Yin et al., "Telphenyl-based helical mimetics that disrupt the p53/HDM2 interaction," *Angew. Chem. Int. Ed.*, 44:2704-2707, 2005.

Zander et al., "Effect of 6-week course of glucagon-like peptide 1 on glycaemic control, insulin sensitivity, and beta-cell function in type 2 diabetes: a parallel-group study," *Lancet*, 59:824-830, 2002.

Zhang et al., "New approaches in the treatment of type 2 diabetes," *Curr. Opin. Chem. Biol.*, 4:461-467, 2000.

Office Communication issued in U.S. Appl. No. 13/559,388, dated Nov. 7, 2012.

Office Communication issued in U.S. Appl. No. 13/559,388, dated May 2, 2013.

Office Communication issued in U.S. Appl. No. 13/683,979, dated Jul. 10, 2013.

\* cited by examiner

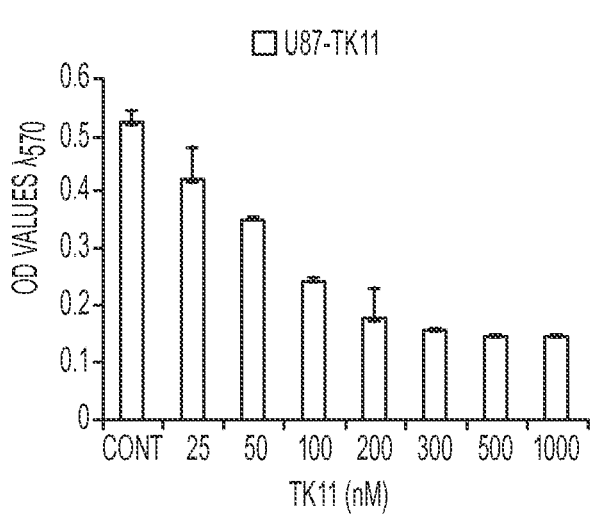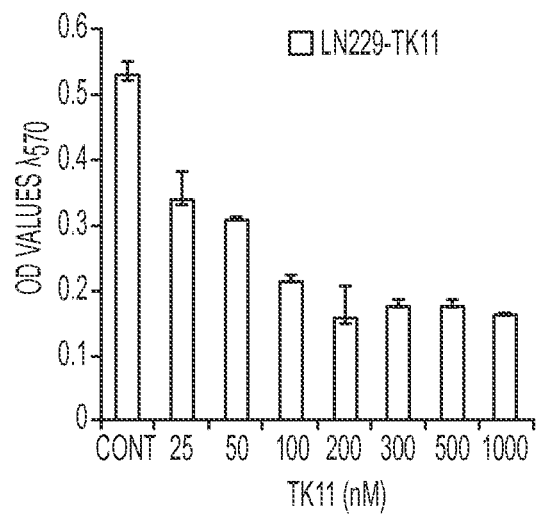
FIG. 8A          FIG. 8B
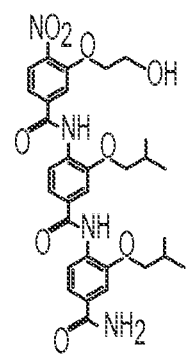
TK11
FIG. 9

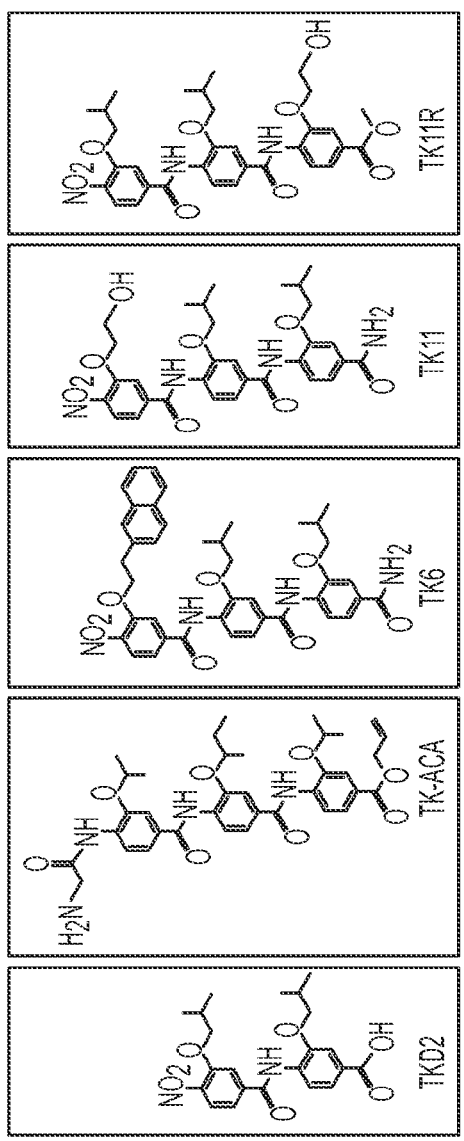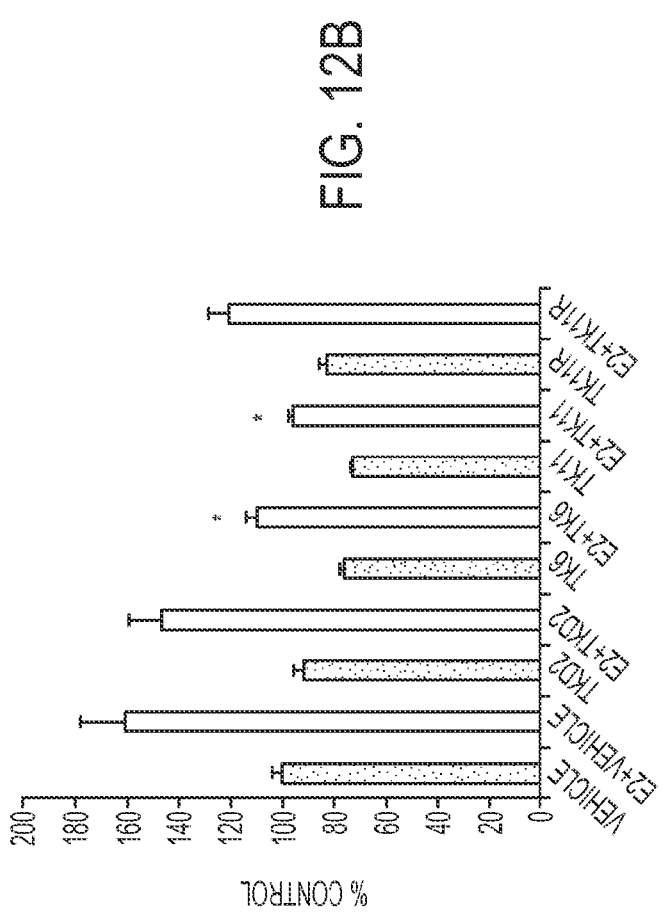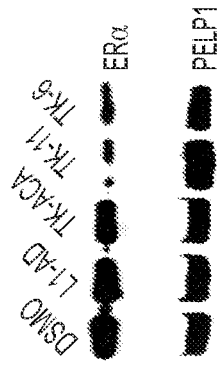

OLIGO-BENZAMIDE COMPOUNDS AND THEIR USE IN TREATING CANCERS

PRIORITY CLAIM

This application claims benefit of priority to U.S. Provisional Application Ser. Nos. 61/563,437, filed Nov. 23, 2011, and 61/664,372, filed Jun. 26, 2012, the entire contents of both applications being hereby incorporated by reference.

FIELD OF THE INVENTION

The present invention relates in general to the field of peptidomimetics and specifically to compositions of matter, kits, methods of making oligo-benzamide peptidomimetic compounds, and methods of their use in prostate cancers.

BACKGROUND OF THE INVENTION

Androgen receptor (AR) signaling is essential for prostate cancer development, growth, and progression at all stages of disease. AR signaling occurs via both genomic and non-genomic pathways and is mediated by AR interaction with cofactors including a scaffolding protein PELP-1. Recently, the inventors have discovered that PELP-1 interacts with AR and that this interaction is critical for both AR-mediated genomic and non-genomic signaling. Thus, they hypothesize that disruption of the interaction of AR and PELP-1 may influence AR-signaling.

Peptidomimetics (also known as peptide mimetics) are small organic molecules that do not possess the peptide backbone structure, however still retain a capability to interact with the same target protein by arranging essential functional groups (i.e., pharmacophores) in a required three-dimensional pattern complimentary to a binding pocket in the protein. Since peptides and proteins adopt and utilize secondary structures (e.g., α-helix, β-sheet, and reverse turns) to make their global shapes and to recognize their binding partners, rational design of secondary structure mimetics is an important strategy in developing small molecule modulators for protein complex formation, compared to conventional high-throughput screening of a chemical library.

At present, no compounds are known that specifically inhibit the interaction with PELP-1 and AR. The identification of such compounds, and assessment of their use as anti-cancer agents, would therefore be highly desirable.

SUMMARY OF THE INVENTION

The present inventors recognized a need for stable small molecules possessing the capability to modulate AR signaling without the limitations of the peptide structure. The present invention provides a class of small molecules that are stable and capable of interacting with molecules involved in AR signaling but lacking the limitations of the peptide structure. These small molecules include α-helix mimetics that represent helical segments in the target molecules.

The oligo-benzamide peptidomimetic compound includes at least three optionally substituted benzamides, with each of the substituted benzamides having one substituent on a benzene ring. The oligo-benzamide peptidomimetic compound modulates protein-protein, protein-peptide, or protein-drug interaction to exert a variety of physiological consequences.

The present invention provides, in one aspect, a compound of formula (I or II):

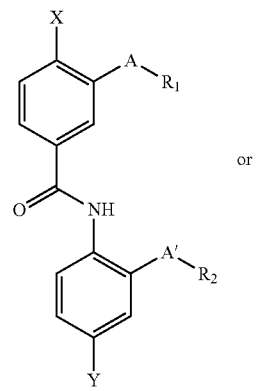

(I)

or

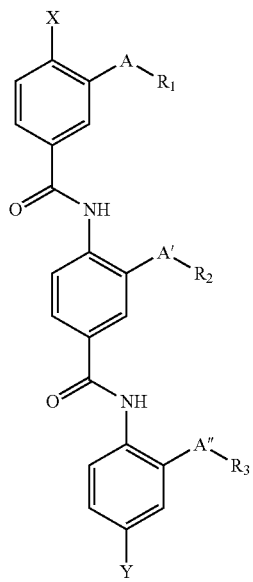

(II)

wherein:
$R_1$, $R_2$ and $R_3$ are each independently H, $C_1$-$C_{10}$ alkyl, $C_1$-$C_{10}$ alkenyl, $C_1$-$C_{10}$ alkynyl, $C_1$-$C_{15}$ optionally substituted arylalkyl, —$(CH_2)_n$—COOR, —$(CH_2)_n$—CONRR', —$(CH_2)_n$—NRR', —$(CH_2)_n$—NH(C=NH)NRR', —$(CH_2)_n$—NRCOR', —$(CH_2)_n$—NRCOOR', —$(CH_2)_n$—OR, —$(CH_2)_n$—SR, —$(CH_2)_n$—SO$_m$R, —$(CH_2)_n$—PO$_m$R, wherein n and m may be any number between 0 and 6 and R and R' may be a H, $C_1$—$C_{10}$ alkyl, $C_1$-$C_{10}$ alkenyl, $C_1$-$C_{10}$ alkynyl, or $C_1$-$C_{15}$ optionally substituted arylalkyl group or

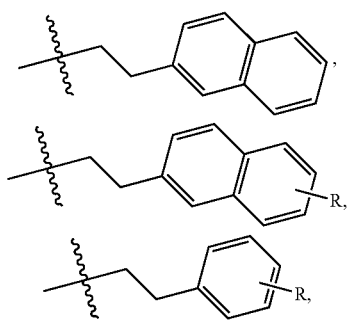

-continued

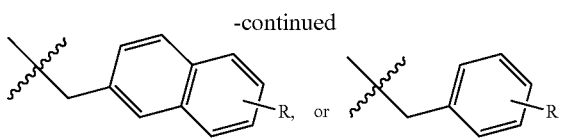

wherein R is independently a H, $C_{1-10}$ alkyl, $C_{1-10}$ alkenyl, $C_{1-10}$ alkynyl, $C_{1-15}$ optionally substituted arylalkyl, hydroxyl, $C_{1-10}$ alkoxy, amino, $C_{1-10}$ monoalkylamino, $C_{1-10}$ dialkylamino, guanidine, nitro, carboxylic acid, $C_{1-10}$ alkylcarbonyl, $C_{1-15}$ arylcarbonyl, halogen, sulfhydryl, $C_{1-10}$ alkylsulfenyl, $C_{1-10}$ alkylsulfinyl, $C_{1-10}$ alkylsulfonyl, sulfonic acid, sulfate, phosphenyl, phosphinyl, phosphonic acid, phosphate group;

X is a H, —$NO_2$, —NRR', —NRCOR', —NRCOOR', —NRCONR', —OR, —SR, —COR, —COOR, —CONRCOR' wherein R and R' are independently H, —$CH_2$—Z', $C_1$-$C_{10}$ alkyl, $C_1$-$C_{10}$ alkenyl, $C_1$-$C_{10}$ alkynyl, or $C_1$-$C_{15}$ arylalkyl, each of which is optionally substituted with —COOR", —CONR"R'", —NR"R'", —NH(C=NH)NR'R'", —NR" COR'", —NR"COOR'", —OR", —SR", —$SO_nR$", or —$PO_nR$", wherein n may be any number between 0 and 6 and R" and R'" may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group, and wherein Z' is:

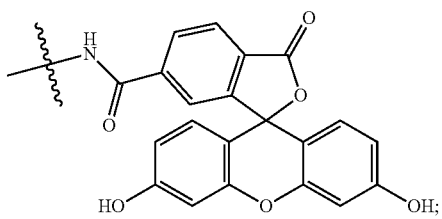 [SMILES: *NC(=O)c1ccc2c(c1)C1(OC2=O)c2ccc(O)cc2Oc2cc(O)ccc21]

and
Y is —$(CH_2)_n COOR_4$, —$(CH_2)_n CONR_4R_5$, —$(CH_2)_n NR_4R_5$, —$(CH_2)_n$—$NR_4R_5$, —$(CH_2)_n$—NH(C=NH)$NR_4R_5$, —$(CH_2)_n$—$NR_4COR_5$, —$(CH_2)_n$—$NR_4COOR_5$, —$(CH_2)$—$NR_4CONR_5$, —$(CH_2)_n$—$OR_4$, —$(CH_2)_n$—$SR_4$, —$(CH_2)_n$—$SO_mR_4$, —$(CH_2)_n$—$PO_mR_4$, wherein n and m may be any number between 0 and 6, $R_4$ and $R_5$ are independently selected from —H, $C_1$-$C_{10}$ alkyl, $C_1$-$C_{10}$ alkenyl, $C_1$-$C_{10}$ alkynyl, or $C_1$-$C_{15}$ optionally substituted arylalkyl group; and A, A' and A" are independently —O—, —S—, —NR—, —$(CH_2)$n—, —CO— wherein n may be any number between 1-6.

Where X is —$NO_2$, A, A' and A" may each be O, or $R_1$, $R_2$ and $R_3$ may independently be $C_{1-10}$ alkyl, $C_{1-10}$ hydroxyalkyl, $C_{1-10}$ alkenyl or $C_1$-$C_{15}$ arylalkyl, or A, A' and A" may each be O and $R_1$, $R_2$ and $R_3$ and may independently be $C_{1-10}$ alkyl, $C_{1-10}$ hydroxyalkyl, $C_{1-10}$ alkenyl or $C_1$-$C_{15}$ arylalkyl. Also where X is —$NO_2$, A, A' and A" may each be O, or $R_1$, $R_2$ and $R_3$ may independently be $C_{1-10}$ alkyl or $C_{1-10}$ hydroxyalkyl, or A, A' and A" may each be O, and $R_1$, $R_2$ and $R_3$ may independently be $C_{1-10}$ alkyl or $C_{1-10}$ hydroxyalkyl.

Where Y is $COOCH_3$, A, A' and A" may each be NH or $R_1$, $R_2$ and $R_3$ may independently be $C_{1-10}$ alkyl, $C_{1-10}$ hydroxyalkyl, $C_{1-10}$ alkenyl or $C_1$-$C_{15}$ arylalkyl, or A, A' and A" may each be NH and $R_1$, $R_2$ and $R_3$ may independently be $C_{1-10}$ alkyl, $C_{1-10}$ hydroxyalkyl, $C_{1-10}$ alkenyl or $C_1$-$C_{15}$ arylalkyl. Also where Y is $COOCH_3$, A, A' and A" may each be NH, or $R_1$, $R_2$ and $R_3$ may independently be $C_{1-10}$ alkyl or $C_{1-10}$ hydroxyalkyl, or A, A' and A" may each be NH, and $R_1$, $R_2$ and $R_3$ may independently be $C_{1-10}$ alkyl or $C_{1-10}$ hydroxyalkyl.

Where X is —$NO_2$ and Y is —$C(O)NH_2$, A, A' and A" may each be O, or $R_1$, $R_2$ and $R_3$ may independently be $C_{1-10}$ alkyl, $C_{1-10}$ hydroxyalkyl, $C_{1-10}$ alkenyl or $C_1$-$C_{15}$ arylalkyl, or A, A' and A" may each be O, and $R_1$, $R_2$ and $R_3$ may independently be $C_{1-10}$ alkyl, $C_{1-10}$ hydroxyalkyl, $C_{1-10}$ alkenyl or $C_1$-$C_{15}$ arylalkyl. Also where X is —$NO_2$ and Y is —$C(O)NH_2$, A, A' and A" may each be O, or $R_1$, $R_2$ and $R_3$ may independently be $C_{1-10}$ alkyl or $C_{1-10}$ hydroxyalkyl, or A, A' and A" may each be O, and $R_1$, $R_2$ and $R_3$ may independently be $C_{1-10}$ alkyl or $C_{1-10}$ hydroxyalkyl.

In particular, the compound may have a formula selected from:

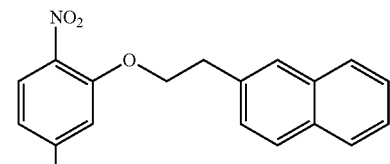
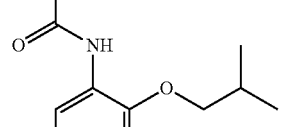
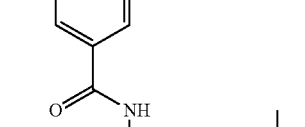
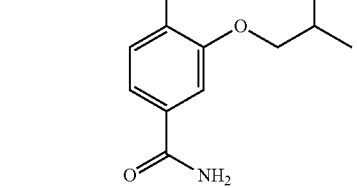
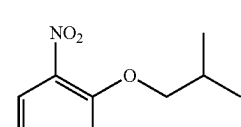
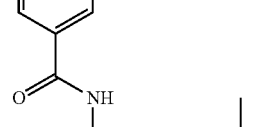
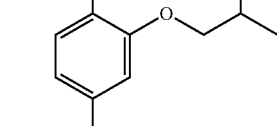
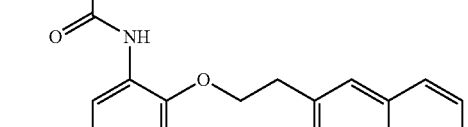
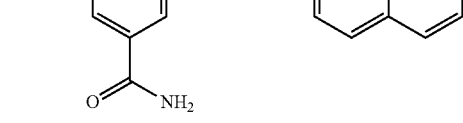

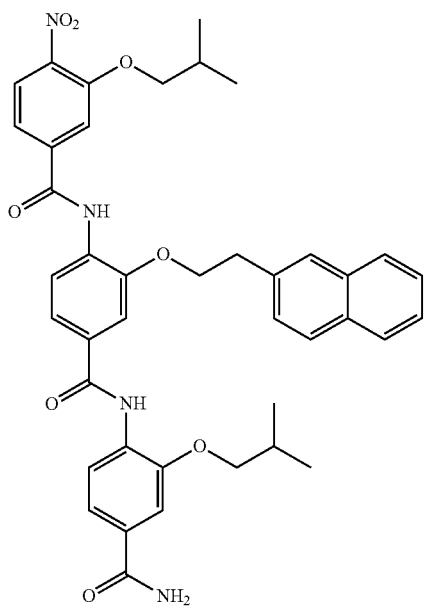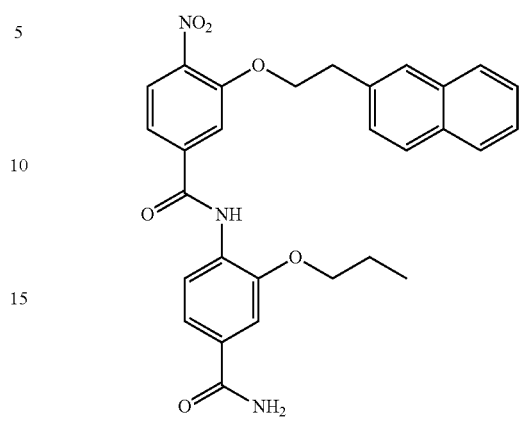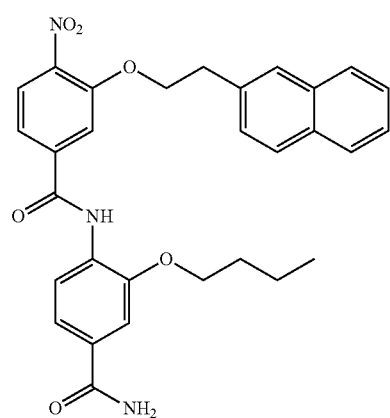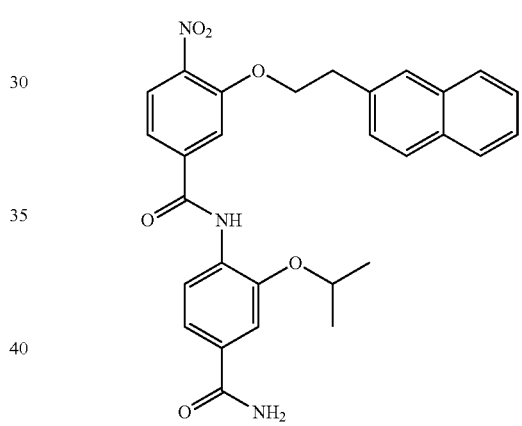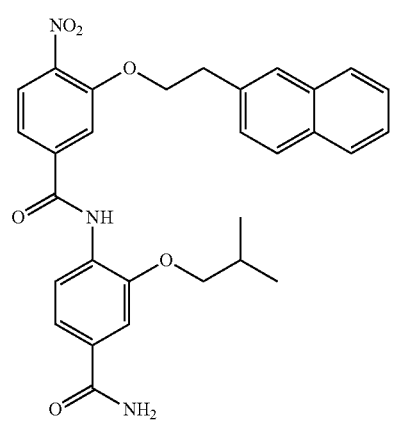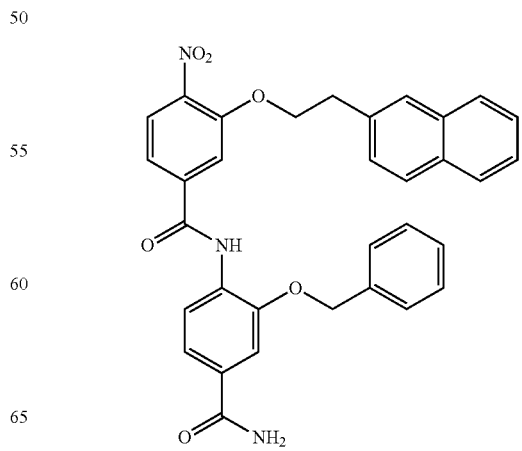

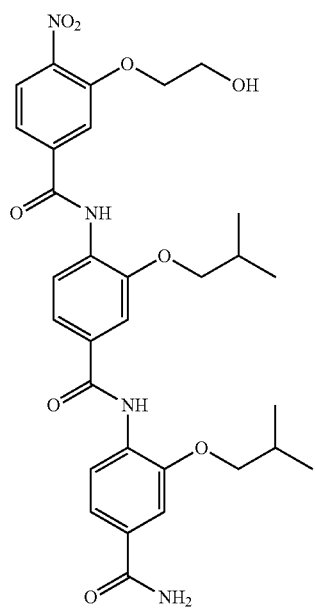
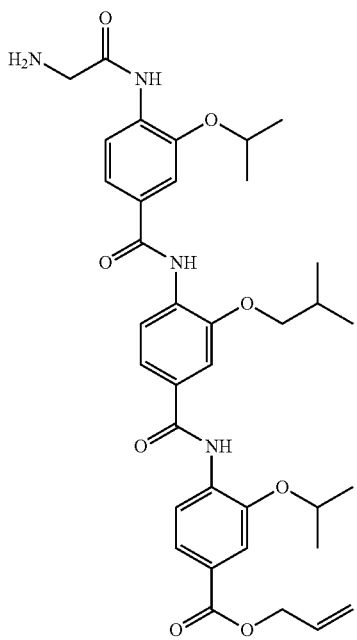
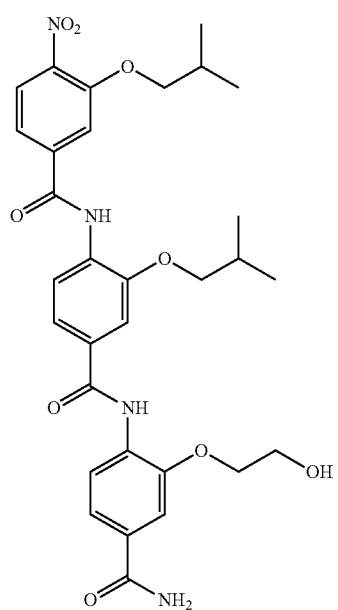
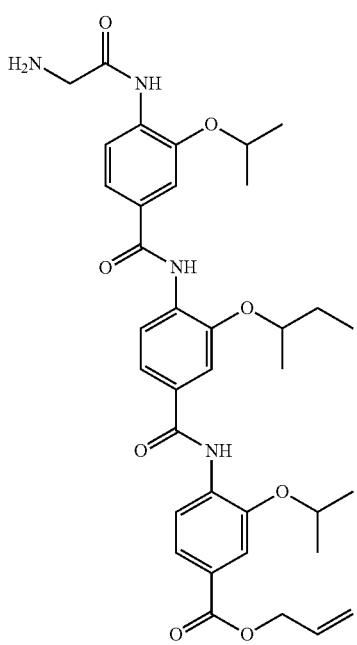

-continued

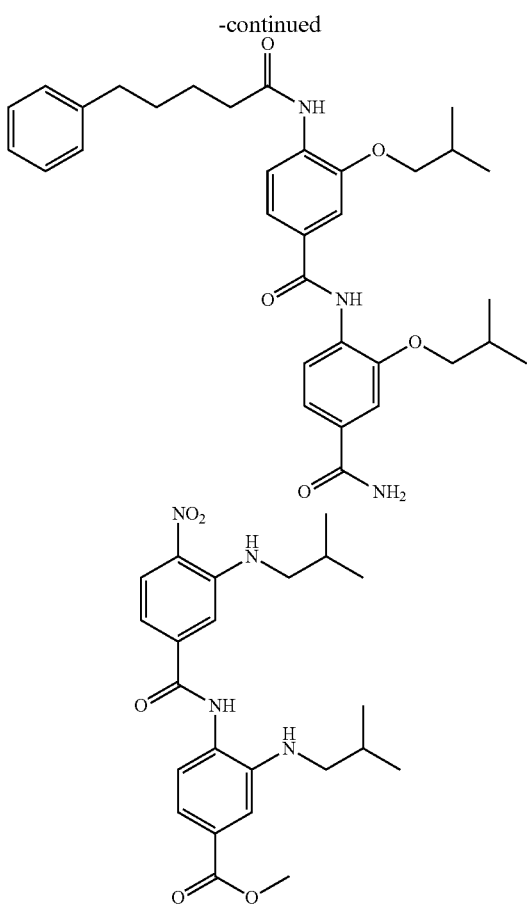

In another embodiment, there is provided a method of inhibiting a prostate, cell in a subject comprising administering to said subject a therapeutically sufficient amount of an oligo-benzamide peptidomimetic compound as shown above. The tumor cell may be an androgen receptor (AR)- or estrogen receptor (ER)-positive tumor cell. The tumor cell may be a carcinoma cell. Administering may comprise local, regional, systemic, or continual administration. The peptidomimetic compound may be is fused to a cell delivery domain. Inhibiting may comprise inducing growth arrest of said tumor cell, apoptosis of said tumor cell and/or necrosis of a tumor tissue comprising said tumor cell. The method may further comprise providing to said subject a second anti-cancer therapy, such as surgery, chemotherapy, radiotherapy, hormonal therapy, toxin therapy, immunotherapy, and cryotherapy. The second anti-cancer therapy may provided prior to administering said compound, after administering said compound, or at the same time as said compound. The subject may be a human. The compound may be administered at about 0.1 to about 100 mg/kg, or at about 1 to about 50 mg/kg. The compound may be administered daily, such as daily for 7 days, 2 weeks, 3 weeks, 4 weeks, one month, 6 weeks, 8 weeks, two months, 12 weeks, or 3 months. The compound may be is administered weekly, such as weekly for 2 weeks, 3 weeks, 4 weeks, 6 weeks, 8 weeks, 10 weeks, or 12 weeks. The method may further comprising assessing AR- or ER-driven gene expression in said tumor cell of said subject prior to administering said compound, or further comprising assessing AR- or ER-driven gene expression in said tumor cell of said subject after administering said compound.

Also provided is a pharmaceutical composition comprising a compound as shown above dispersed in a pharmaceutically acceptable carrier, buffer or diluent.

The use of the word "a" or "an" when used in conjunction with the term "comprising" in the claims and/or the specification may mean "one," but it is also consistent with the meaning of "one or more," "at least one," and "one or more than one."

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements. It is contemplated that any method or composition described herein can be implemented with respect to any other method or composition described herein.

BRIEF DESCRIPTION OF THE DRAWINGS

For a more complete understanding of the features and advantages of the present invention, reference is now made to the detailed description of the invention along with the accompanying figures and in which:

(FIG. 1A) Chemical structure of T6. (FIG. 1B) C4-2 cells were transiently transfected with Gal-4-3WxxLF promoter or (FIG. 1C) with synthetic hARGAL4 and the PSAen-hGAL4-luc reporter. Cells were maintained for 48 h in the absence of androgens and with either 100 nM of peptidomimetic or volume equivalent of vehicle (DMSO) control and luciferase activity measured. (FIG. 1D) Peptidomimetics knocked down ligand independent proliferation in C4-2 cells FIGS. 2A-D. Oligobenzamide control of PC3 cell proliferation.

FIGS. 8A-B. Testing of oligo-benzamides for growth inhibitor of two brain cancer cell lines. (FIG. 8A) Results for cell line U87. (FIG. 8B) Results for cell line LN229. Interestingly, TK11 showed weak potency in inhibiting prostate cancer cell line but higher specificity for brain tumor cells.

FIG. 9. Structure of compound TK11.

(FIG. 10A) Results for cell line CH157. (FIG. 10B) Results for cell line IOMM-LEE.

FIGS. 12A-C. Testing of oligo-benzamides for growth inhibition of estrogen driven proliferation. (FIG. 12A) Structure of peptidomimetics used in the assays. (FIG. 12B) Effect of tribenzamimetics on E2 driven proliferation using ZR75 model cells. (FIG. 12C) Effect of tribenzamides on PELP 1-ER interaction. *, P<0.05.

DETAILED DESCRIPTION OF THE INVENTION

Figure 1A:
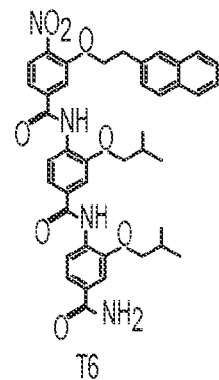
FIGS. 1A-D. Oligobenzamide control of C4-2 cell proliferation.

Tri-benzamide contains three alkyl groups ($R_{1-3}$) that correspond to the i, and i+4 and i+7 positions of a helix. The peptidomimetics of the present invention are non-toxic under in vitro and in vivo conditions. The development of these peptidomimetics represents a quantum leap in the development of a drug to target AR signaling. Interestingly, these synthetic molecules prevent androgen-induced translocation of AR to the nucleus and represents perhaps one of the first instances of peptidomimetic agents that block AR nuclear translocation. In addition to improvements in the helical face and presentation of the leucines, the inventors have proven efficacy of this system against prostate cancer cell proliferation both in vitro and in vivo. Thus, in contrast to existing technology, the inventors have developed and tested active peptidomimetics against breast, brain and ovarian cancers.

These findings are exciting and represent a potentially viable method to target AR signaling pathways in various cancers. These peptidomimetics have advantages of both peptides (e.g., high efficacy and selectivity, low side effects) and small organic molecules (e.g., high enzyme stability, oral bioavailability, effective cell permeability). In addition, the novel platform using the peptidomimetics with a rigid oligo-benzamide backbone allows the presentation of selected amino acid side chains in the proper helical structure that is critical for optimal AR interactions.

I. Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes branched or unbranched hydrocarbon chains, having between about 1-20 carbons, with "lower alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octadecyl and so on. Alkyl includes cycloalkyl, such as cyclopropyl, cyclobutyl, cyclopentyl, and cyclohexyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino, and the like to form alkyl groups such as trifluoro methyl, 3-hydroxyhexyl, 2-carboxypropyl, 2-fluoroethyl, carboxymethyl, cyanobutyl and the like.

As used herein, the term "aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. If not otherwise specified, the group may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, carboxamidyl, alkoxycarbonyl, carbamyl, alkyl, alkenyl, alkynyl, nitro, amino, alkoxy, amido, imino, imido, guanidino, hydrazido, aminoxy, alkoxyamino and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkoxy" includes an optionally substituted straight chain or branched alkyl group having between about 1-50 carbons with a terminal oxygen linking the alkyl group to the rest of the molecule. Alkoxy includes methoxy, ethoxy, propoxy, isopropoxy, butoxy, t-butoxy, pentoxy and so on. If not otherwise specified, alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

For any of the groups above, the modifier Cn-Cn' defines both the minimum and maximum number of carbon atoms for the group. For example, "$C_2$-$C_{10}$ alkyl" designates those alkyl groups having from 2 to 10 carbon atoms (e.g., 2, 3, 4, 5, 6, 7, 8, 9, or 10, or any range derivable therein, e.g., 3 to 10 carbon atoms).

As used herein, the term "pharmaceutically acceptable" means those materials which are useful in preparing a pharmaceutical composition that is generally safe, non-toxic and neither biologically nor otherwise undesirable and includes that which is acceptable for veterinary use as well as human pharmaceutical use.

As used herein, the term "pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

II. Oligo-Benzamides and Methods of Synthesis

The present invention provides synthetic molecules which present the essential functionalities of corresponding peptide ligands in the proper three dimensional orientation that enables specific protein interactions, leading to either stimulation or inhibition of protein-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins (Marshall, 1993; Ahn et al., 2002). Thereby, peptidomimetics potentially combine the advantages of peptides (e.g., high efficacy and selectivity, low side effects) and small organic molecules (e.g., high enzymatic stability and oral bioavailability).

To mimic α-helices, the present invention provides an oligo-benzamide scaffold that is rigid in structure and place and orient substituents as an α-helix does. Substitution on the rigid tris-benzamide, for instance, allowed easy placement of three functional groups ($R_{1-3}$) corresponding to the side chains of amino acids found at the i, i+4, and i+7 positions of an ideal α-helix. Furthermore, the present inventors have developed a facile synthetic route to prepare a number of tris-benzamides to represent α-helical segments of target proteins. U.S. Patent Publication 2009/0012141, incorporated herein by reference, discloses a variety of oligo-benzamide compounds and methods of synthesis therefor.

More specifically, the present invention provides an oligo-benzamide peptidomimetic compound as illustrated includes 2 or 3 optionally substituted benzamides—so called "bis" and "tris" benzamides. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligo-benzamide peptidomimetic compound may be attached to amino acids, oligopeptides, optionally substituted alkyl, or other structures known to the skilled artisan.

The substitution on the substituted benzamide is generally on a benzene ring and may be on the 2, 3, 4, 5, or 6 position of each of the benzene rings. The substitutions may be at the same position on each of the benzamide rings but may also be at different positions on each of the benzene rings. For example, the substitution is connected to the benzamide ring by a chemical linkage including ether, thioether, amine, amide, carbamate, urea, and carbon-carbon (single-, double-, and triple-) bonds, and the substitution comprises optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide peptidomimetic compound that includes at least two optionally substituted benzamides, with each of the substituted benzamides having one substitution on a benzene ring. The substitutions are individually attached to the benzene rings of the oligo-benzamide peptidomimetic compound by a chemical linkage including ether, thioether, amine, amide, carbamate, urea, and carbon-carbon (single-, double-, and triple-) bonds. The substitutions generally include optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

U.S. Patent Publication 2009/0012141 provides synthesis schemes to prepare α-helix mimetic compounds of the present invention, for example, in FIG. 2 therein. A specific example in that document provides fifteen α-helix mimetic compounds made starting with a 4-amino-3-hydroxybenzoic acid compound 7, which was converted to an N—Ac protected methyl ester compound 8. Various alkyl groups were introduced to the hydroxyl group using a variety of alkyl halides and a base (e.g., NaOH) known to the skilled artisan. After the alkylation reaction, the methyl ester compound 9 was hydrolyzed using a base (like LiOH), and methyl 4-amino-3-hydroxybenzoate compound 10 was coupled to the free benzoic acid using a coupling reagent (like BOP), resulting in a benzamide compound II containing one alkyl group corresponding to the i position of a helix. These steps were repeated to synthesize oligo-benzamide compounds. Those of skill in the art would understand the broader applicability of such methods in the synthesis of other compounds such as those disclosed herein.

III. Pharmaceutical Formulations and Methods of Treatment

A. Formulations and Routes of Administration

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The pharmaceutical peptidomimetic composition includes a therapeutically effective amount of an oligo-benzamide peptidomimetic compound or a salt, a solvent, or a derivative thereof based on an oligo-benzamide peptidomimetic compound, and one or more pharmaceutically acceptable carriers. For example, the bis- or tris-benzamide peptidomimetic composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical peptidomimetic compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

B. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999. However underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening test have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

C. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes serous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed. A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancers and certain populations (e.g., Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e., preventative, oophorectomy after completion of childbearing. Australia being member of International Cancer Genome Consortium is leading efforts to map ovarian cancer's complete genome.

Ovarian cancer at its early stages (I/II) is difficult to diagnose until it spreads and advances to later stages (III/IV). This is because most symptoms are non-specific and thus of little use in diagnosis. When an ovarian malignancy is included in the list of diagnostic possibilities, a limited number of laboratory tests are indicated. A complete blood count (CBC) and serum electrolyte test should be obtained in all patients. The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor. A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfil these criteria. However in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However, the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives—the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind ["optimal debulking"]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed. Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected. The five-year survival rate for all stages of ovarian cancer is 45.5%. For cases where a diagnosis is made early in the disease, when the cancer is still confined to the primary site, the five-year survival rate is 92.7%.

D. Brain Cancer

A brain tumor is an intracranial solid neoplasm, a tumor (defined as an abnormal growth of cells) within the brain or the central spinal canal. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells), lymphatic tissue, blood vessels), in the cranial nerves, in the brain envelopes (meninges), skull, pituitary and pineal gland, or spread from cancers primarily located in other organs (metastatic tumors).

Any brain tumor is inherently serious and life-threatening because of its invasive and infiltrative character in the limited space of the intracranial cavity. However, brain tumors (even malignant ones) are not invariably fatal. Brain tumors or intracranial neoplasms can be cancerous (malignant) or non-cancerous (benign); however, the definitions of malignant or benign neoplasms differs from those commonly used in other types of cancerous or non-cancerous neoplasms in the body. Its threat level depends on the combination of factors like the type of tumor, its location, its size and its state of development. Because the brain is well protected by the skull, the early detection of a brain tumor only occurs when diagnostic tools are directed at the intracranial cavity. Usually detection occurs in advanced stages when the presence of the tumor has caused unexplained symptoms.

Primary (true) brain tumors are commonly located in the posterior cranial fossa in children and in the anterior two-thirds of the cerebral hemispheres in adults, although they can affect any part of the brain.

The prognosis of brain cancer varies based on the type of cancer. Medulloblastoma has a good prognosis with chemotherapy, radiotherapy, and surgical resection while glioblastoma multiforme has a median survival of only 12 months even with aggressive chemoradiotherapy and surgery. Brainstem gliomas have the poorest prognosis of any form of brain cancer, with most patients dying within one year, even with therapy that typically consists of radiation to the tumor along with corticosteroids. However, one type of brainstem glioma, a focal seems open to exceptional prognosis and long-term survival has frequently been reported.

Glioblastoma multiforme is the deadliest and most common form of malignant brain tumor. Even when aggressive multimodality therapy consisting of radiotherapy, chemotherapy, and surgical excision is used, median survival is only 12-17 months. Standard therapy for glioblastoma multiforme consists of maximal surgical resection of the tumor, followed by radiotherapy between two and four weeks after the surgical procedure to remove the cancer. This is followed by chemotherapy. Most patients with glioblastoma take a corticosteroid, typically dexamethasone, during their illness to palliate symptoms. Experimental treatments include gamma-knife radiosurgery, boron neutron capture therapy and gene transfer.

Oligodendroglioma is an incurable but slowly progressive malignant brain tumor. They can be treated with surgical resection, chemotherapy, and/or radiotherapy. For suspected low-grade oligodendrogliomas in select patients, some neuro-oncologists opt for a course of watchful waiting, with only symptomatic therapy. Tumors with the 1p/19q co-deletion have been found to be especially chemosensitive, and one source reports oligodendrogliomas to be among the most chemosensitive of human solid malignancies. A median survival of up to 16.7 years has been reported for low grade oligodendrogliomas.

Although there is no specific or singular clinical symptom or sign for any brain tumors, the presence of a combination of symptoms and the lack of corresponding clinical indications of infections or other causes can be an indicator to redirect diagnostic investigation towards the possibility of an intracranial neoplasm.

The diagnosis will often start with an interrogation of the patient to get a clear view of his medical antecedents, and his current symptoms. Clinical and laboratory investigations will serve to exclude infections as the cause of the symptoms. Examinations in this stage may include ophtamological, otolaryngological (or ENT) and/or electrophysiological exams. The use of electroencephalography (EEG) often plays a role in the diagnosis of brain tumors.

Swelling, or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilatation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Imaging plays a central role in the diagnosis of brain tumors. Early imaging methods—invasive and sometimes dangerous—such as pneumoencephalography and cerebral angiography, have been abandoned in recent times in favor of non-invasive, high-resolution techniques, such as computed tomography (CT)-scans and especially magnetic resonance imaging (MRI). Neoplasms will often show as differently colored masses (also referred to as processes) in CT or MRI results.

Benign brain tumors often show up as hypodense (darker than brain tissue) mass lesions on cranial CT-scans. On MRI, they appear either hypo- (darker than brain tissue) or isointense (same intensity as brain tissue) on T1-weighted scans, or hyperintense (brighter than brain tissue) on T2-weighted MRI, although the appearance is variable.

Contrast agent uptake, sometimes in characteristic patterns, can be demonstrated on either CT or MRI-scans in most malignant primary and metastatic brain tumors. Perifocal edema, or pressure-areas, or where the brain tissue has been compressed by an invasive process also appears hyperintense on T2-weighted MRI might indicate the presence a diffuse neoplasm (unclear outline). This is because these tumors disrupt the normal functioning of the blood-brain barrier and lead to an increase in its permeability. However it is not possible to diagnose high versus low grade gliomas based on enhancement pattern alone.

Glioblastoma multiforme and anaplastic astrocytoma have been associated with the genetic acute hepatic porphyrias (PCT, AIP, HCP and VP), including positive testing associated with drug refractory seizures. Unexplained complications associated with drug treatments with these tumors should alert physicians to an undiagnosed neurological porphyria.

The definitive diagnosis of brain tumor can only be confirmed by histological examination of tumor tissue samples obtained either by means of brain biopsy or open surgery. The histological examination is essential for determining the appropriate treatment and the correct prognosis. This examination, performed by a pathologist, typically has three stages: interoperative examination of fresh tissue, preliminary microscopic examination of prepared tissues, and followup examination of prepared tissues after immunohistochemical staining or genetic analysis.

When a brain tumor is diagnosed, a medical team will be formed to assess the treatment options presented by the leading surgeon to the patient and his/her family. Given the location of primary solid neoplasms of the brain in most cases a "do-nothing" option is usually not presented. Neurosurgeons take the time to observe the evolution of the neoplasm before proposing a management plan to the patient and his/her relatives. These various types of treatment are available depending on neoplasm type and location and may be combined to give the best chances of survival: surgery: complete or partial ressection of the tumor with the objective of removing as many tumor cells as possible; radiotherapy; and chemotherapy, with the aim of killing as many as possible of cancerous cells left behind after surgery and of putting remaining tumor cells into a nondividing, sleeping state for as long as possible.

Survival rates in primary brain tumors depend on the type of tumor, age, functional status of the patient, the extent of surgical tumor removal and other factors specific to each case.

The primary and most desired course of action described in medical literature is surgical removal (resection) via craniotomy. Minimally invasive techniques are being studied but are far from being common practice. The prime remediating objective of surgery is to remove as many tumor cells as possible, with complete removal being the best outcome and cytoreduction ("debulking") of the tumor otherwise. In some cases access to the tumor is impossible and impedes or prohibits surgery.

Many meningiomas, with the exception of some tumors located at the skull base, can be successfully removed surgically. Most pituitary adenomas can be removed surgically, often using a minimally invasive approach through the nasal cavity and skull base (trans-nasal, trans-sphenoidal approach). Large pituitary adenomas require a craniotomy (opening of the skull) for their removal. Radiotherapy, including stereotactic approaches, is reserved for inoperable cases.

Several current research studies aim to improve the surgical removal of brain tumors by labeling tumor cells with a chemical (5-aminolevulinic acid) that causes them to fluoresce. Post-operative radiotherapy and chemotherapy are integral parts of the therapeutic standard for malignant tumors. Radiotherapy may also be administered in cases of "low-grade" gliomas, when a significant tumor burden reduction could not be achieved surgically.

Any person undergoing brain surgery may suffer from epileptic seizures. Seizures can vary from absences to severe tonic-clonic attacks. Medication is prescribed and administered to minimize or eliminate the occurrence of seizures.

Multiple metastatic tumors are generally treated with radiotherapy and chemotherapy rather than surgery. The prognosis in such cases is determined by the primary tumor, but is generally poor.

The goal of radiation therapy is to selectively kill tumor cells while leaving normal brain tissue unharmed. In standard external beam radiation therapy, multiple treatments of standard-dose "fractions" of radiation are applied to the brain. This process is repeated for a total of 10 to 30 treatments, depending on the type of tumor. This additional treatment provides some patients with improved outcomes and longer survival rates.

Radiosurgery is a treatment method that uses computerized calculations to focus radiation at the site of the tumor while minimizing the radiation dose to the surrounding brain. Radiosurgery may be an adjunct to other treatments, or it may represent the primary treatment technique for some tumors.

Radiotherapy may be used following, or in some cases in place of, resection of the tumor. Forms of radiotherapy used for brain cancer include external beam radiation therapy, brachytherapy, and in more difficult cases, stereotactic radiosurgery, such as Gamma knife, Cyberknife or Novalis Tx radiosurgery.

Radiotherapy is the most common treatment for secondary brain tumors. The amount of radiotherapy depends on the size of the area of the brain affected by cancer. Conventional external beam 'whole brain radiotherapy treatment' (WBRT) or 'whole brain irradiation' may be suggested if there is a risk that other secondary tumors will develop in the future. Stereotactic radiotherapy is usually recommended in cases involving fewer than three small secondary brain tumors.

Patients undergoing chemotherapy are administered drugs designed to kill tumor cells. Although chemotherapy may improve overall survival in patients with the most malignant primary brain tumors, it does so in only about 20 percent of patients. Chemotherapy is often used in young children instead of radiation, as radiation may have negative effects on the developing brain. The decision to prescribe this treatment is based on a patient's overall health, type of tumor, and extent of the cancer. The toxicity and many side effects of the drugs, and the uncertain outcome of chemotherapy in brain tumors puts this treatment further down the line of treatment options with surgery and radiation therapy preferred.

A shunt is used not as a cure but to relieve symptoms by reducing hydrocephalus caused by blockage of cerebrospinal fluid.

Researchers are presently investigating a number of promising new treatments including gene therapy, highly focused radiation therapy, immunotherapy and novel chemotherapies. A variety of new treatments are being made available on an investigational basis at centers specializing in brain tumor therapies.

E. Prostate Cancer

Prostate cancer is a disease in which cancer develops in the prostate, a gland in the male reproductive system. In 2007, almost 220,000 new cases were reported, and over 27,000 deaths were attributed to this malignancy. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. However, many men who develop prostate cancer never have symptoms, undergo no therapy, and eventually die of other causes. Many factors, including genetics and diet, have been implicated in the development of prostate cancer.

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cutoff, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL (nanograms per milliliter) are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastasize.

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Clalis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as y and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine$^{125}$ or palladium$^{103}$) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Anti-androgens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of down-regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so anti-androgens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium[89], phosphorus[32], or samarium[153], also target bone metastases and may help relieve pain.

High Intensity Focused Ultrasound (HIFU) for prostate cancer utilizes ultrasonnic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

Several medications and vitamins may also help prevent prostate cancer. Two dietary supplements, vitamin E and selenium, may help prevent prostate cancer when taken daily. Estrogens from fermented soybeans and other plant sources (called phytoestrogens) may also help prevent prostate cancer. The selective estrogen receptor modulator drug toremifene has shown promise in early trials. Two medications which block the conversion of testosterone to dihydrotestosterone, finasteride and dutasteride, have also shown some promise. As of 2006 the use of these medications for primary prevention is still in the testing phase, and they are not widely used for this purpose. The problem with these medications is that they may preferentially block the development of lower-grade prostate tumors, leading to a relatively greater chance of higher grade cancers, and negating any overall survival improvement. Green tea may be protective (due to its polyphenol content), though the data is mixed. A 2006 study of green tea derivatives demonstrated promising prostate cancer prevention in patients at high risk for the disease. In 2003, an Australian research team led by Graham Giles of The Cancer Council Australia concluded that frequent masturbation by males appears to help prevent the development of prostate cancer. Recent research published in the Journal of the National Cancer Institute suggests that taking multivitamins more than seven times a week can increase the risks of contracting the disease. This research was unable to highlight the exact vitamins responsible for this increase (almost double), although they suggest that vitamin A, vitamin E and beta-carotene may lie at its heart. It is advised that those taking multivitamins never exceed the stated daily dose on the label. Scientists recommend a healthy, well balanced diet rich in fiber, and to reduce intake of meat. A 2007 study published in the Journal of the National Cancer Institute found that men eating cauliflower, broccoli, or one of the other cruciferous vegetables, more than once a week were 40% less likely to develop prostate cancer than men who rarely ate those vegetables. Scientists believe the reason for this phenomenon has to do with a phytochemical called Diindolylmethane in these vegetables that has antiandrogenic and immune modulating properties. This compound is currently under investigation by the National Cancer Institute as a natural therapeutic for prostate cancer.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Model Cells. Human Breast cancer cells MCF7, ZR75, glioma cells U87, T98G, LN229, and the ovarian cancer cell line SKOV3 were obtained from the American Type Culture Collection (ATCC) and were maintained using ATCC recommended media.

Cell Proliferation Assays. Cell proliferation rates were measured by using MTT Cell Viability Assay in 96-well micro plates. Model cells were seeded in 96-well plates ($2\times10^3$ cells/well) in DMEM or RPMI medium containing 10% serum. After an overnight incubation, cells were treated with varying concentrations of oligo-benzamides for 72 h and growth inhibition was determined by using traditional MTT assay (Sigma) following manufacturer's instructions.

Estrogen Mediated Proliferation Assays. MCF7, ZR75 model cell lines were synchronized to G0/G1 phase by serum starvation for 3 days in 0.5% dextran charcoal-treated serum containing medium and released into cell cycle by addition of $10^{-8}$ M $E_2$ in the presence or absence of TK11 Cell proliferation rate was measured in 96-well format using CellTiter-Glo Luminescent Cell Viability Assay (Promega) following manufacturer's instructions.

Therapy Resistance Assays. Tamoxifen (Tam) therapy resistant MCF7-HER2 and MCF7-TAM cells were cultured in tamoxifen (10-7M) containing media in the presence or absence of TK11 and proliferation was measured by MTT assay (Sigma) following manufacturer's instructions.

Migration Assays. Models cells MCF7 and MCF7-PELP1 were cultured in steroid free medium for two days, treated with E2 (10-8M) in the presence or absence of TK11 (500 nM) and cell migration potential was analyzed using a Boyden chamber assay (Promega) as per manufacturer instructions.

Reporter Gene Assays. Model cells were seeded in 6-well plates. After overnight incubation, the cells were transfected with ERE-Luc+ER plasmids using fugene for 6 h. Then, 24 h after transfection, cells were treated with vehicle or TK11 for an additional 24 h. Each transfection was carried out in triplicate and normalized with the β-gal activity and total protein concentration. Luciferase activity was measured by using the luciferase assay system (Promega, Madison, WI).

Binding Assays. Purified commercially available estrogen receptor (ER) was incubated with biotin-con or biotin-TK11 peptidomimetic in the presence of estrogen (E2). TK11 interaction with ER was determined using avidin immunoprecipitation (IP) followed by western blotting. For some experiments, MCF-7 cells were stimulated with estrogen (E2), nuclear lysates were prepared and incubated with biotin-con or biotin-TK11 peptidomimetic. TK11 interactions with endogenous ER were analyzed by avidin IP. For some experiments, purified ER, GST-PELP1 was incubated in the presence of E2 and ability of control or TK11 (500 nM) to compete PELP1 interaction with ER was determined GST pull down assay.

Results

Ligand independent activation of the androgen receptor (AR) may involve (1) AR mutants or splicing variants that lack a ligand-binding domain (LBD) such ARv7 or (2) have gain of function mutation in AR (largely occurring in the LBD and conferring ligand promiscuity or in constitutively active conformation) or (3) undergo activation by other cofactors or receptors. AR interacts with several protein cofactors such as the scaffolding protein PELP1 (Proline-, glutamic acid-, and leucine-rich), heat shock proteins (Hsp-27, Hsp-90), and others that are involved in AR nuclear translocation and activation of both genomic and non-genomic signals[1]. The network of interactions between AR and its protein cofactors is critical for AR signaling both in ligand dependent and indepenent pathways. Disruption of interactions between AR and critical cofactors by targeting structural motifs involved in protein-protein interactions (PPIs) may block both ligand dependent and indepenent activation of AR and represent a novel therapeutic approach for patients with castrate resistant prostate cancer (CRPC).

In the castrate state, CRPC cells grow in an androgen depleted environment. Recently, splice variants of the AR that lack the ligand binding domain (LBD) have been shown to be dramatically upregulated in CRPC and appear to be the primary driver of androgen-responsive genes in CRPC. AR splice variants include the commonly seen ARv7 and AR567. Since these splice variants lack the LBD, they contain the N-terminus of AR and are ligand indepenent. These splice variants are thus not affected by agents targeting the LBD of AR, including all strategies aimed at androgen deprivation and newer agents in development including MDV3100. There is a critical and unmet need for agents targeting the N-terminus of the AR.

In an elegant study, Dehm et al. (2007) molecularly dissected the TAU5 domain in the N-terminus of the AR and showed that the $^{435}$WxxLF$^{439}$ motif on AR was fully responsible for its ligand indepenent activity. Mechanistically, WxxLF did not rely on an interaction with the AR LBD to mediate ligand independent AR activity. Rather, WxxLF functioned as an autonomous transactivation domain. While the overall structure of the N-terminus of AR is poorly understood, the identification of this specific protein motif on AR enables potential targeting of PPIs involved in ligand indepenent activation of AR. Thus, small molecule inhibitors for the interaction of critical cofactors with the WxxLF motif on the AR may block ligand indepenent AR-mediated signaling pathways.

Figure 1B:
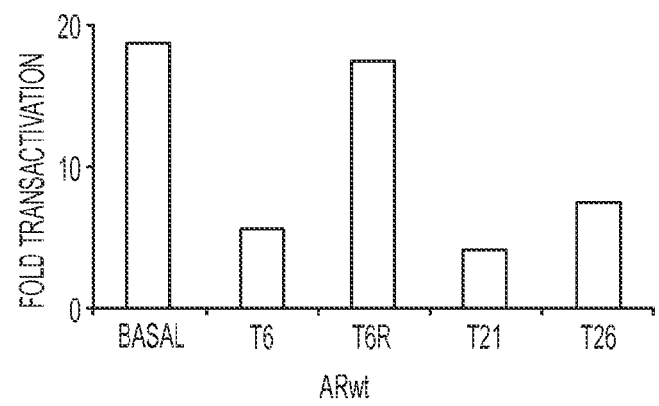
Figure 1C:
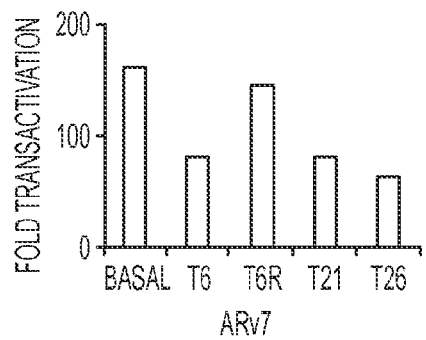
Figure 1D:
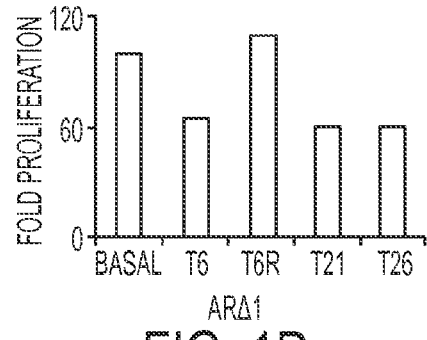

Ligand indepenent activation involves the WxxLF motif, whose tertiary structure has not been crystallographically resolved. Indeed, binding partners of AR through this WxxLF motif have not been determined. Modeling of the WxxLF motif suggests that this motif may adopt an α-helical structure. Based on this model, the inventors designed three peptidomimetics T6, T21 and T26 to mimic the $^{435}$WxxLF$^{439}$ motif on AR and to target PPIs through this domain (FIG. 1A). The screening strategy involved the use of synthetic Gal-4-3WxxLF (Gal4 reporter driven by 3 copies of the WxxLF motif) (FIG. 1B) and AR-Gal4 constructs (wt AR with its DNA binding domain replaced by Gal4 DNA binding domain) (from Dr. Dehm, U. Minnesota) (FIG. 1C) in LNCaP cells. T21, T26, or T6 (but not the control T6R) knocked down the basal ligand indepenent transcription from this WxxLF driven promoters. Further, these peptidomimetics abrogated ligand independent proliferation of C4-2 cells (FIG. 1D).

Figure 2A:
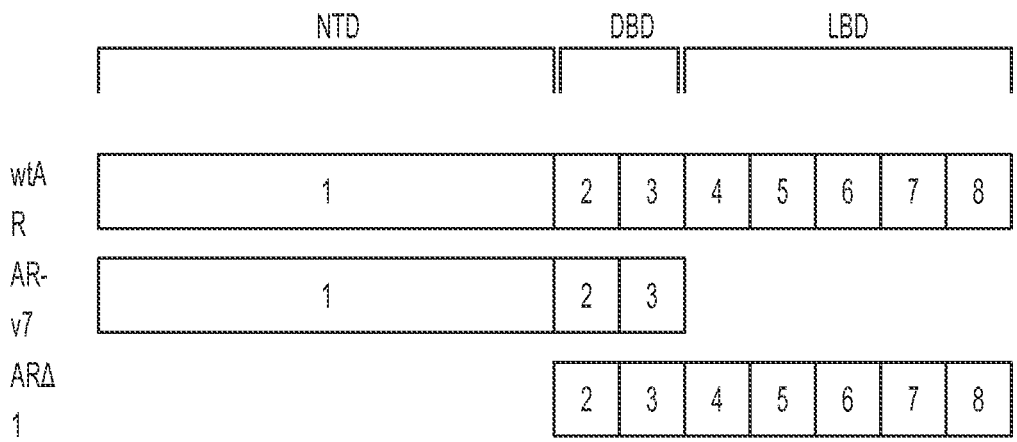
(FIG. 2A) Structure of AR deletion mutants with numbered exons (FIG. 2B) Effect of D2 and T6 on basal (AI) and AD transcription. PC-3 cells were transiently transfected with ARE-luciferase along with plasmids expressing ARwt (FIG. 2B), ARv7 (FIG. 2C) or ARΔ1 (FIG. 2D). Cells were maintained for 48 h either without (EtOH) or with (1 nM DHT) and in the presence of 100 nM of peptidomimetic or volume equivalent of vehicle (DMSO) control. Luciferase assay results are shown. Data is normalized to the basal level of expression with AR wt in PC3 cells.
Figure 2B:
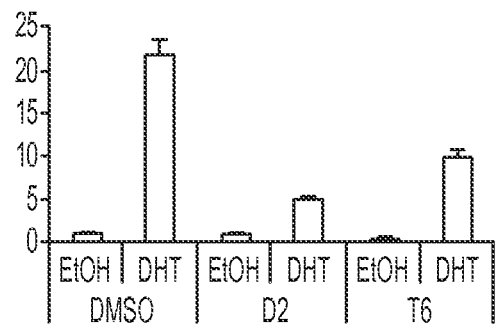
Figure 2C:
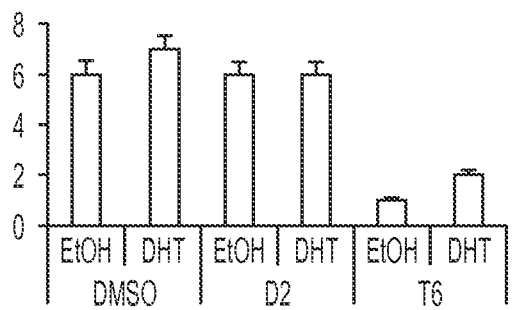
Figure 2D:
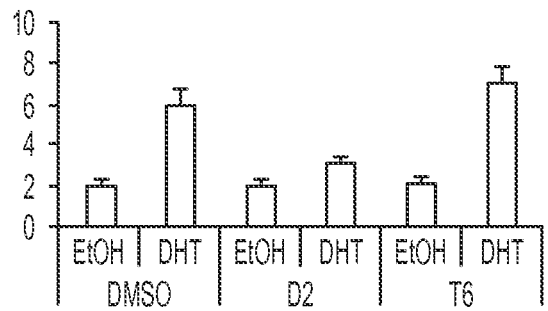

Since the WxxLF motif is also present in the truncated forms of the androgen receptor, the inventors then evaluated the ability of the peptidomimetics to block ARv7-driven transcription from a minimal ARE luciferase reporter. In PC-3 (AR-ve) cells, T6 and D2 were able to suppress Ligand dependent transcription mediated by ARwt (FIG. 2B). Interestingly, T6 but not D2 was able to block ARv7-mediated transcription (FIG. 2C). T6 was not able to block ARΔ1-mediated transcription (ARΔ1 lacks AR exon 1 and thus the WxxLF motif). These findings were confirmed with a synthetic AR with point mutations in the WxxLF motif (data not shown). AR in CWR22v1 cells, which have both ARwt and ARv7, T6 was able to suppress both the basal and DHT-induced transcription from a minimal ARE luciferase (FIG. 2D).

Figure 3A:
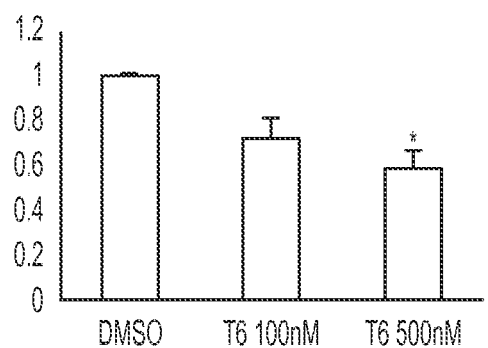
FIGS. 3A-B. Effect of T6 on basal transcription driven by splice variants. PC-3 cells were transiently transfected with ARE-luciferase along with plasmids expressing ARv7 (FIG. 3A) or AR567 (FIG. 3B). Cells were maintained for 48 h either without (EtOH) or with (1 nM DHT) and in the presence of 100 nM of peptidomimetic or volume equivalent of vehicle (DMSO) control. Luciferase assay results are shown. Data is normalized to the basal level of expression with AR wt in PC3 cells.
Figure 3B:
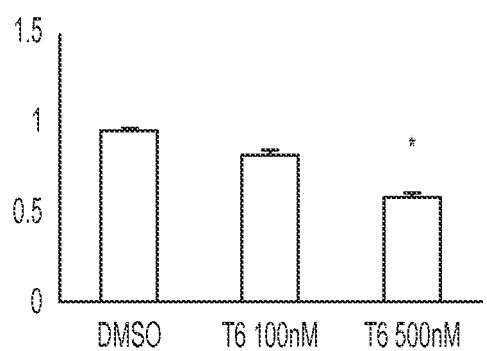

The inventors have also shown that T6 decreases the transcription driven by both the ARv7 and AR567 splice variants (FIGS. 3A-B). These data validate the efficacy of these agents in a dose dependent manner.

Figure 4:
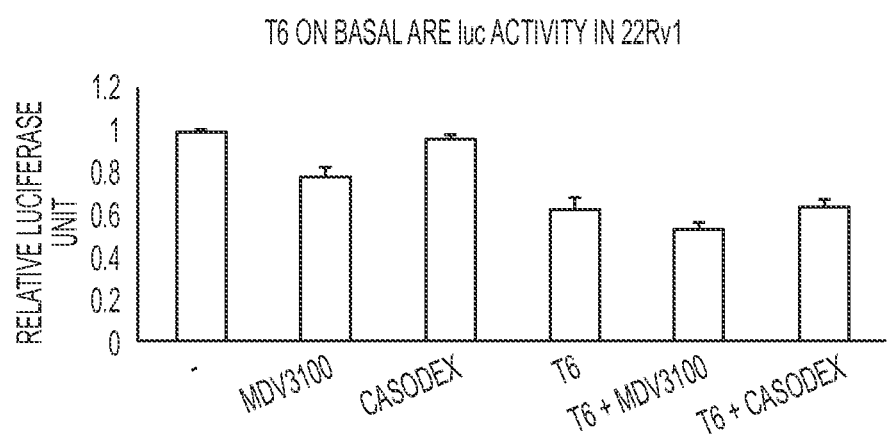
FIG. 4. Effect of T6 on basal level of ARE expression in CWR22v1 cells. CWR22v1 cells were transiently transfected with ARE-luciferase. Cells were maintained for 48 h without (EtOH) and in the presence of 100 nM of peptidomimetic or volume equivalent of vehicle (DMSO) control or 10 µM of casodex or MDV3100. Luciferase assay results are shown.

To further validate the importance of these peptidomimetics, the inventors used the CWR22v1 cells that have both the wtAR and the splice variants co-expressed. In CWR22v1 cells, the basal level of transcription is driven by ARv7 splice variant and the androgen induced level of transcription is driven by ARwt. T6 abrogated the basal level of transcription driven by the ARv7 (FIG. 4). This is significant as neither casodex nor MDV3100 could significantly affect the basal ARE activity in CWR22v1 cells. These data indicate that T6 has functional activities that agents targeting the AR do not have.

Figure 5:
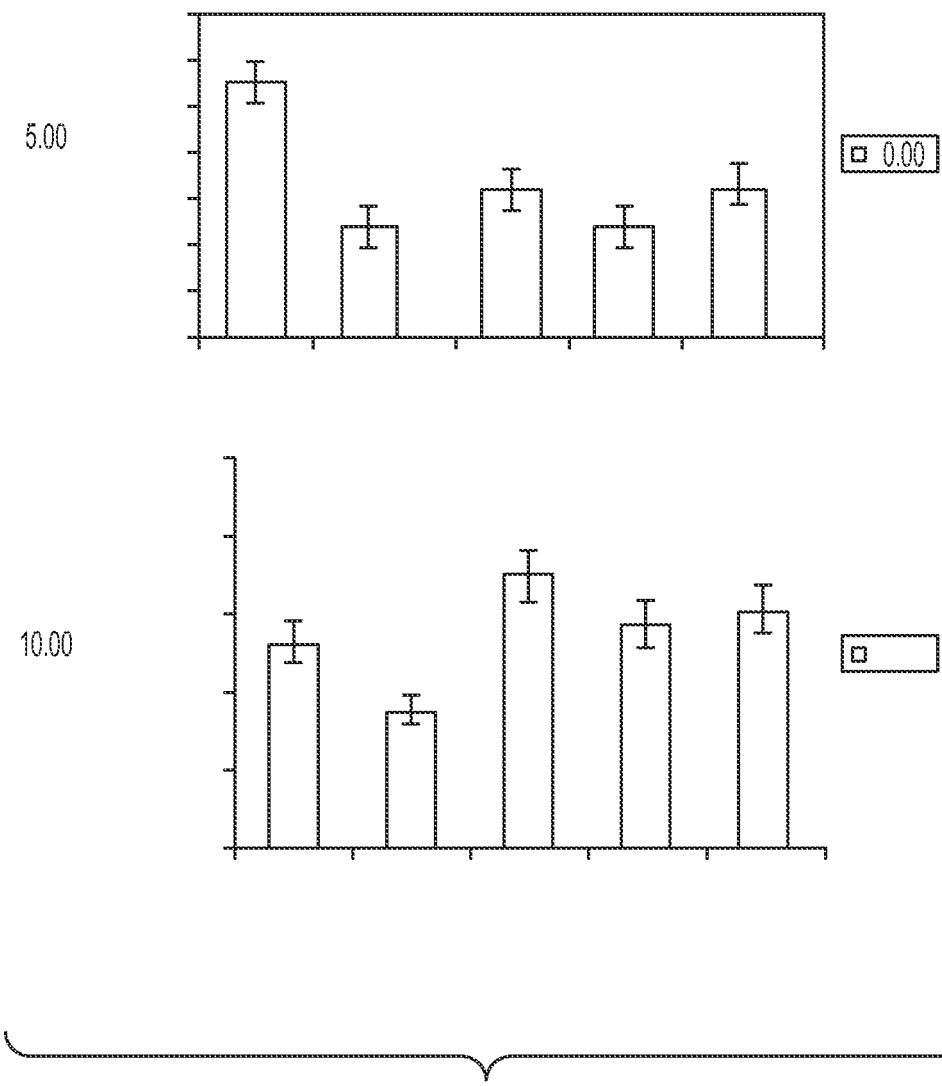
FIG. 5. Effect of T6 on basal level of ARE expression in M12 cells. M12 cells were transiently transfected with the rat probasin-luciferase reporter and either ARwt or ARv7. Cells were maintained for 48 h without (EtOH) and in the presence of 100 nM of peptidomimetic or volume equivalent of vehicle (DMSO) control or 10 µM of MDV3100. Luciferase assay results are shown.

These data were independently confirmed by evaluating the effect of T6 in the M12 cells (FIG. 5) and reveal that again T6 is able to independently knock down the expression of a rat probasin reporter in M12 cells driven by either wtAR or ARv7. These data strongly indicate that T6 in multiple systems is able to independently shut down the transcriptional activity of the AR splice variants.

Finally, confirmation of the role of T6 in modulating ARv7 driven transcription was obtained by evaluation of the gene expression of ARv7 regulated genes. Q-PCR analyses reveal that T6 is able to abrogate the expression of a panel of newly discovered ARv7 regulated genes that MDV3100 or casodex alone could not affect (data not shown). These data strongly support the role for further development of T6 as a novel agent in prostate cancer.

These data indicate the early success of our strategy in targeting both LD and ligand independent genomic activation of the AR and validate our peptidomimetic approach to block AR function in CRPC.

Figure 6:
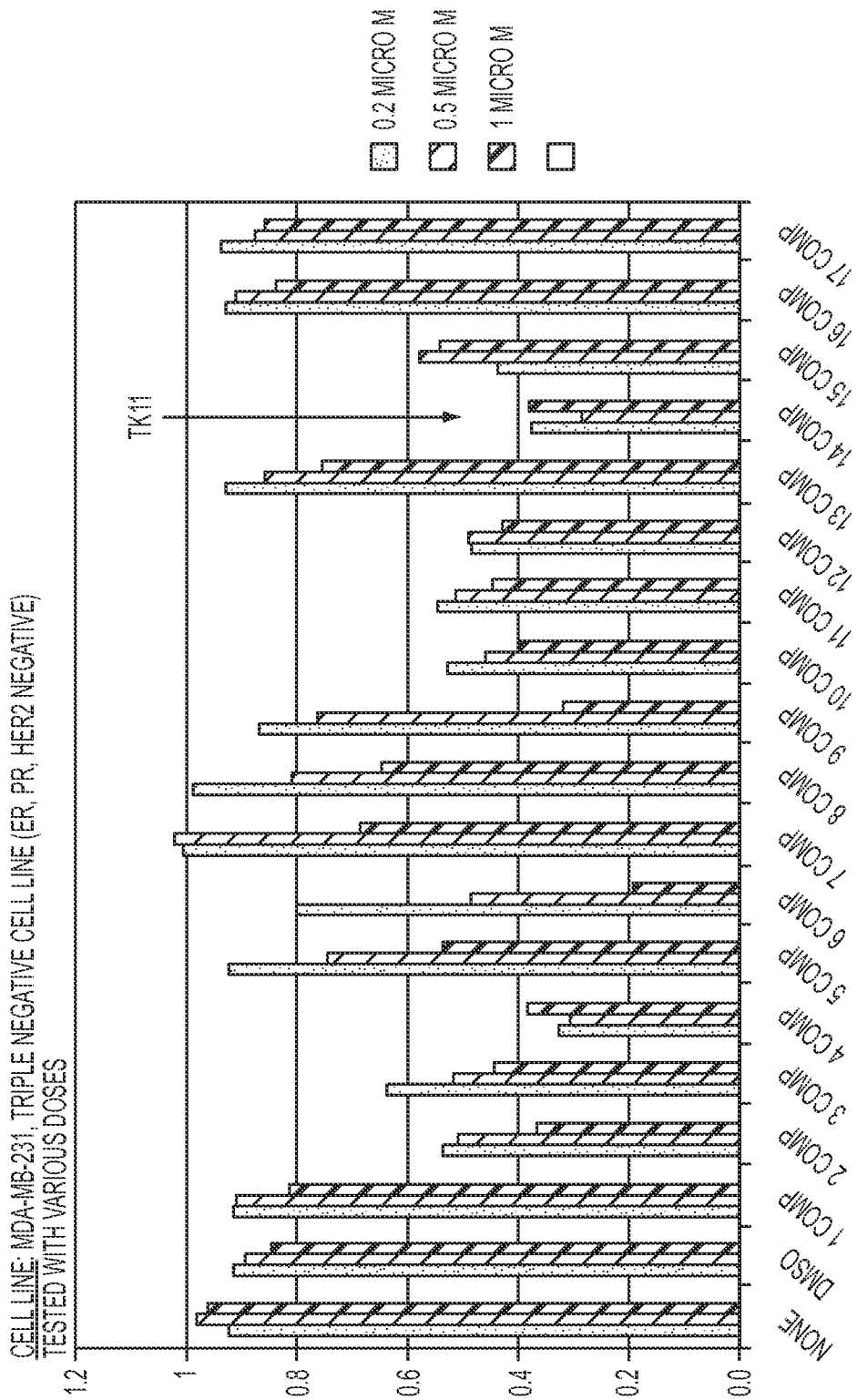
FIG. 6. Testing of oligo-benzamides for growth inhibition of breast cell lines. Interestingly, TK11 showed weak potency in inhibiting prostate cancer cell line but higher specificity for breast tumor cells.
Figure 7:
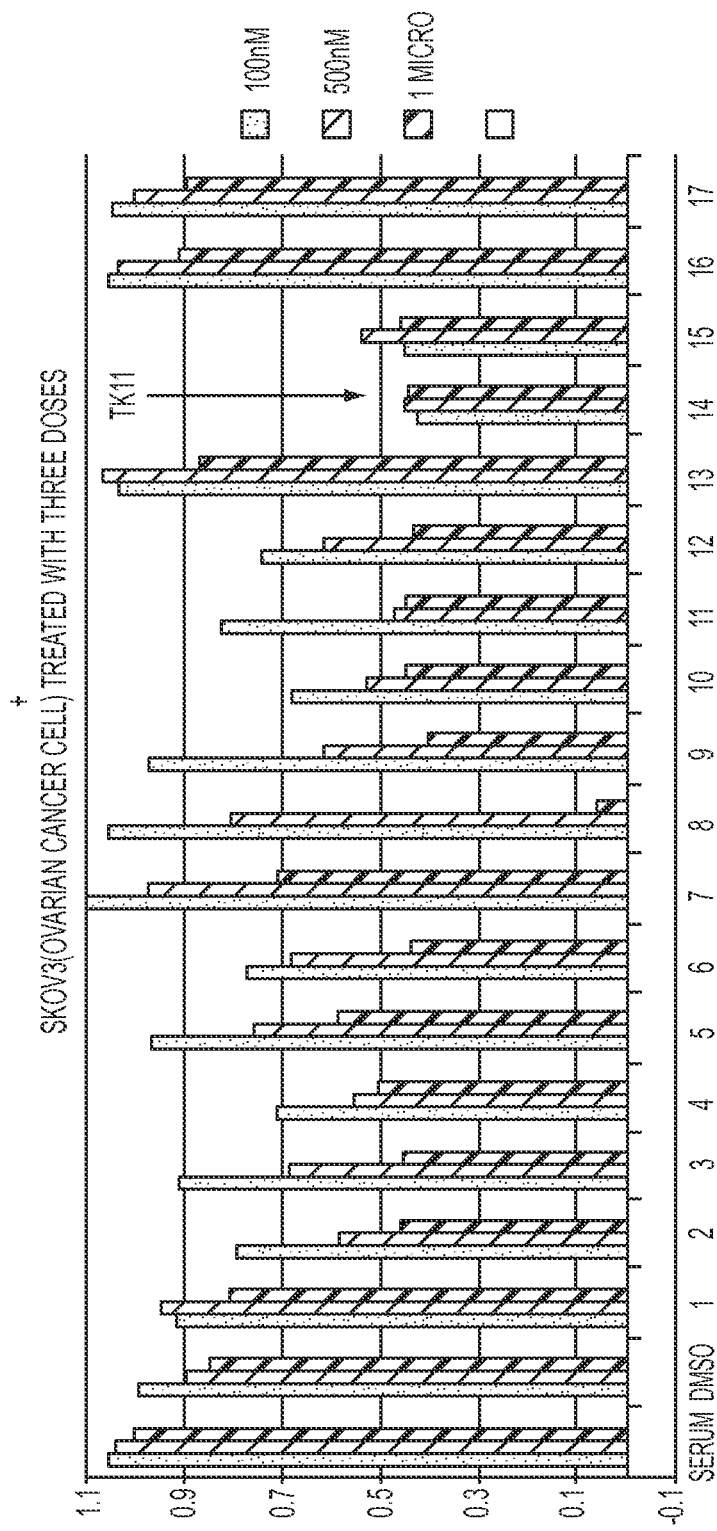
FIG. 7. Testing of oligo-benzamides for growth inhibition of ovarian cell lines. Interestingly, TK11 showed weak potency in inhibiting prostate cancer cell line but higher specificity for ovarian tumor cells.

In order to extend the applicability of these compounds beyond prostate cancer, the inventors tested a number of oligo-benzamides on breast cancer, ovarian cancer, and brain cancer cell lines. Several compounds showed high efficacy showing potent growth inhibition of these cancer cell lines. In particular, the compound called TK11 (FIG. 9) showed high potencies on triple negative breast cancer cell line (FIG. 6), which is the target of intensive research in breast cancer field. And, this compound also showed high potency in ovarian cancer cell line (FIG. 7) and brain cancer cell lines (FIGS. 8A-B).

Figure 10A:
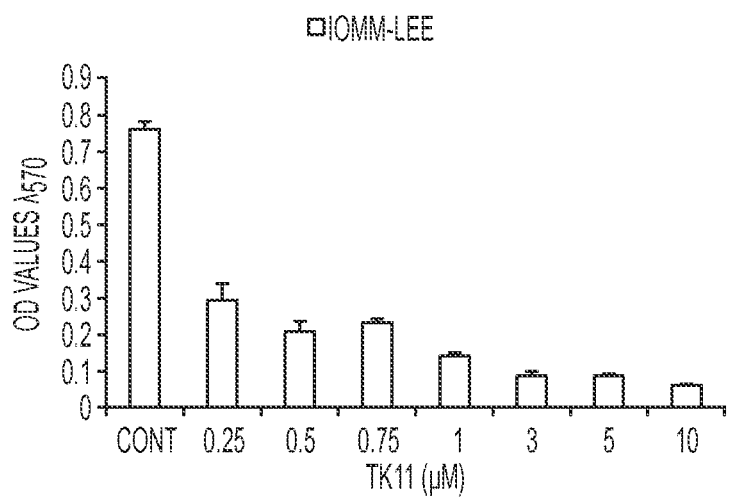
FIGS. 10A-B. Testing of oligo-benzamide (TK 11) for growth inhibitor of two meningioma brain cancer cell lines.
Figure 10B:
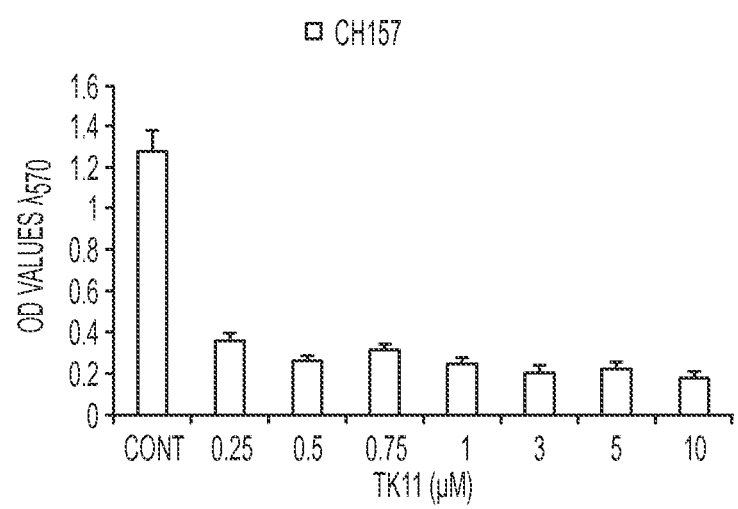
Figure 11:
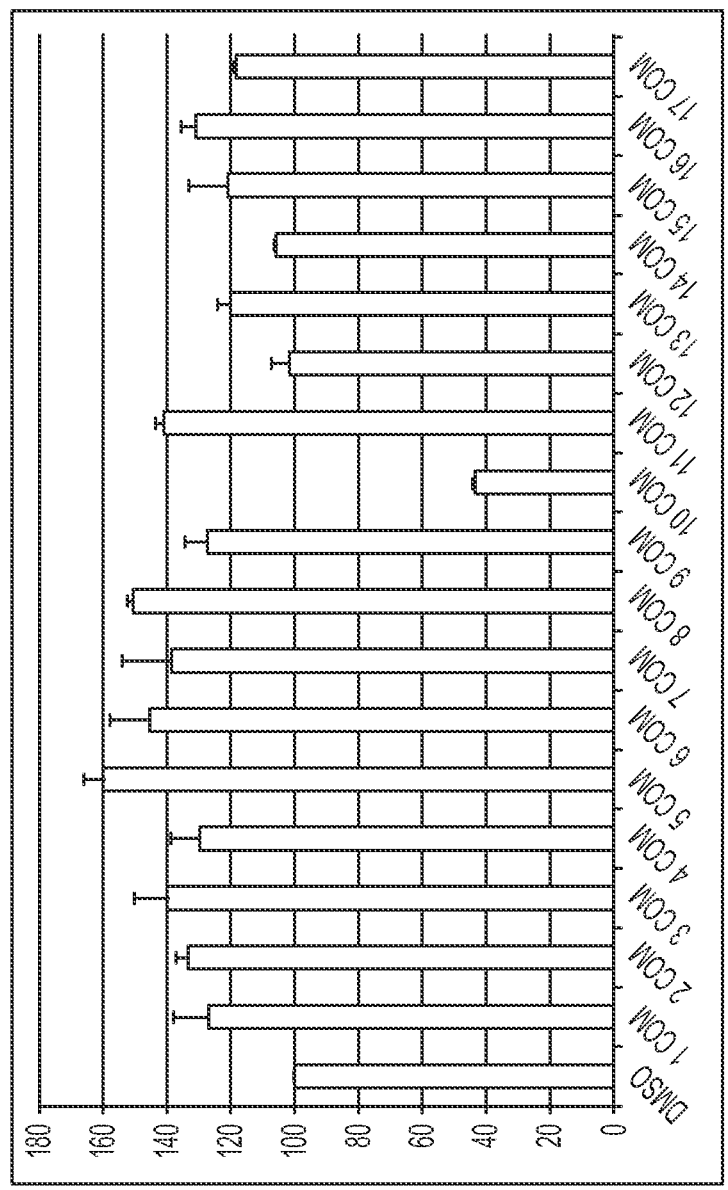
FIG. 11. Testing of oligo-benzamides on growth of normal ovarian cells. IOSE are immortalized normal ovarian cells.

Compounds were tested against other cancer cells lines. FIGS. 10A-B shown the results for TK 11 in an growth inhibition assay on two meningioma brain cancer cell lines. Interestingly, TK11 showed weak potency in inhibiting prostate cancer cell line but higher specificity against for meningioma tumor cells. FIG. 11 shows an assay testing TK11 against ovarian cells. This compound showed weak potency in inhibiting growth of normal ovarian cancer cells, but higher specificity for tumor cells, suggest less side effects.

Figure 13:
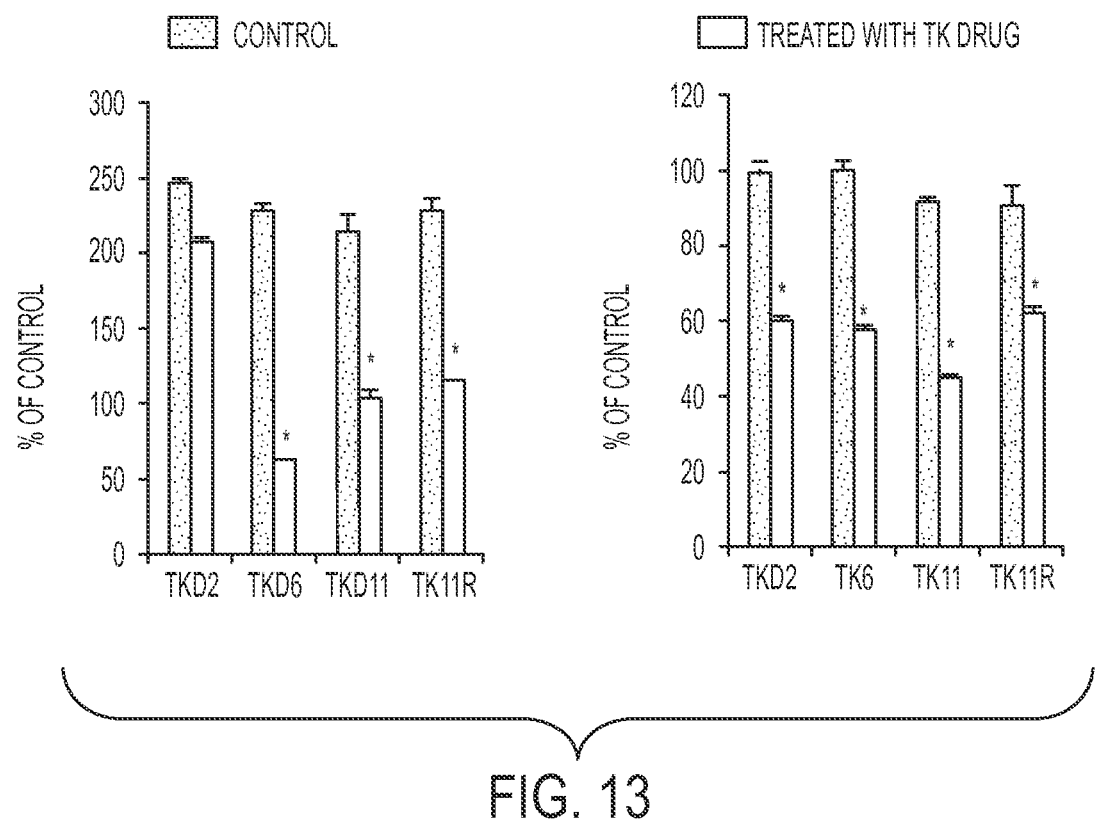
FIG. 13. Testing of oligo-benzamides for growth inhibition of hormonal therapy resistant cells. TK11 significantly inhibited the growth of the resistant cells. *, P <0.05.

FIGS. 12A-C shown the testing of oligo-benzamides for growth inhibition of estrogen driven proliferation. FIG. 12B shows the effect of tribenzamimetics on E2-driven proliferation using ZR75 model cells, while FIG. 12C shows the effect of tribenzamides on PELP1-ER interaction. TK 11 was very efficient in blocking PELP1 oncogene interactions with estrogen receptor. Finally, FIG. 13 shows the testing of oligo-benzamides for growth inhibition of hormonal therapy resistant cells. Interestingly, TK11 significantly inhibited the growth of the resistant cells.

* * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publication 2009/0012141

Dehm et al., *Cancer Res.* 67(20):10067-77, 2007.

What is claimed:

1. A compound of formula (I or II):

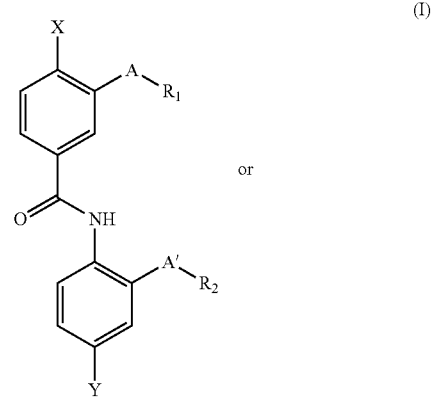

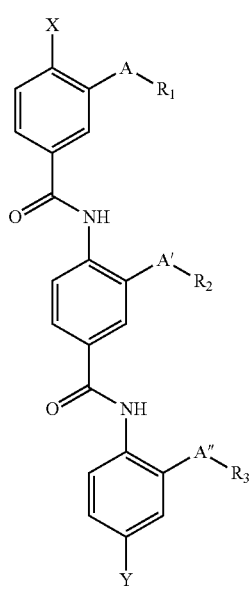

(II)

wherein:
R$_1$, R$_2$ and R$_3$ are each independently H, C$_1$-C$_{10}$ alkyl, C$_1$-C$_{10}$ alkenyl, C$_1$-C$_{10}$ alkynyl, C$_1$-C$_{15}$ optionally substituted arylalkyl, —(CH$_2$)$_n$—COOR, —(CH$_2$)$_n$—CONRR', —(CH$_2$)$_n$—NRR', —(CH$_2$)$_n$—NH(C=NH)NRR', —(CH$_2$)$_n$—NRCOR', —(CH$_2$)$_n$—NRCOOR', —(CH$_2$)$_n$—OR, —(CH$_2$)$_n$—SR, —(CH$_2$)$_n$—SO$_m$R, —(CH$_2$)$_n$—PO$_m$R, wherein n and m may be any number between 0 and 6 and R and R' may be a H, C$_1$-C$_{10}$ alkyl, C$_1$-C$_{10}$ alkenyl, C$_1$-C$_{10}$ alkynyl, or C$_1$-C$_{15}$ optionally substituted arylalkyl group or

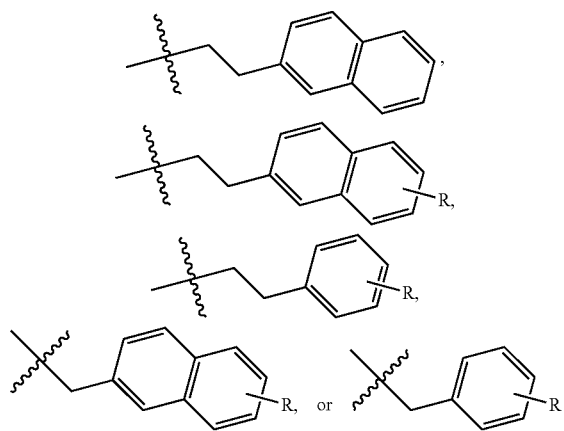

wherein R is independently a H, C$_{1-10}$ alkyl, C$_{1-10}$ alkenyl, C$_{1-10}$ alkynyl, C$_{1-15}$ optionally substituted arylalkyl, hydroxyl, C$_{1-10}$ alkoxy, amino, C$_{1-10}$ monoalkylamino, C$_{1-10}$ dialkylamino, guanidine, nitro, carboxylic acid, C$_{1-10}$ alkylcarbonyl, C$_{1-15}$ arylcarbonyl, halogen, sulfhydryl, C$_{1-10}$ alkylsulfenyl, C$_{1-10}$ alkylsulfinyl, C$_{1-10}$ alkylsulfonyl, sulfonic acid, sulfate, phosphenyl, phosphinyl, phosphonic acid, phosphate group;
X is
Y is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$,—(CH$_2$)—NR$_4$CONR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, C$_1$-C$_{10}$ alkyl, C$_1$-C$_{10}$ alkenyl, C$_1$-C$_{10}$ alkynyl, or C$_1$-C$_{15}$ optionally substituted arylalkyl group; and A, A' and A" are independently —O—, —S—, —NR—, —(CH$_2$)$_n$—, —CO— wherein n may be any number between 1-6.

2. The compound of claim 1, wherein Y is —C(O)NH$_2$.

3. The compound of claim 1, wherein A, A' and A" are each O.

4. The compound of claim 1, wherein R$_1$, R$_2$ and R$_3$ are independently C$_{1-10}$ alkyl, C$_{1-10}$ hydroxyalkyl, C$_{1-10}$ alkenyl or C$_1$-C$_{15}$ arylalkyl.

5. The compound of claim 3, wherein R$_1$, R$_2$ and R$_3$ are independently C$_{1-10}$ alkyl, C$_{1-10}$ hydroxyalkyl, C$_{1-10}$ alkenyl or C$_1$-C$_{15}$ arylalkyl.

6. The compound of claim 1, wherein R$_1$, R$_2$ and R$_3$ are independently C$_{1-10}$ alkyl or C$_{1-10}$ hydroxyalkyl.

7. The compound of claim 3, wherein R$_1$, R$_2$ and R$_3$ are independently C$_{1-10}$ alkyl or C$_{1-10}$ hydroxyalkyl.

8. The compound of claim 1, wherein Y is COOCH$_3$.

9. The compound of claim 1, wherein A, A' and A" are each NH.

10. The compound of claim 8, wherein A, A' and A" are each NH.

11. The compound of claim 8, wherein R$_1$, R$_2$ and R$_3$ are independently C$_{1-10}$ alkyl, C$_{1-10}$ hydroxyalkyl, C$_{1-10}$ alkenyl or C$_1$-C$_{15}$ arylalkyl.

12. The compound of claim 10, wherein R$_1$, R$_2$ and R$_3$ are independently C$_{1-10}$ alkyl or C$_{1-10}$ hydroxyalkyl.

13. The compound of claim 1, having the formula selected from:

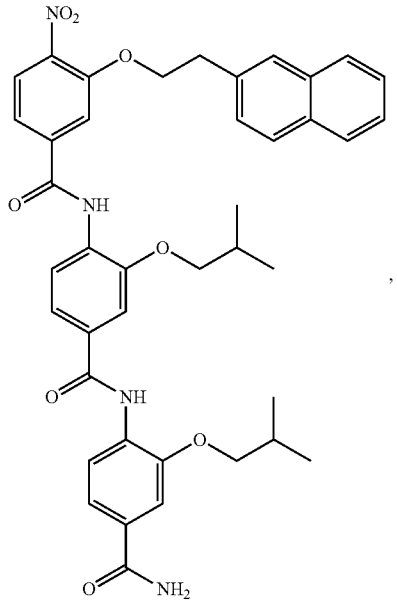

45
-continued
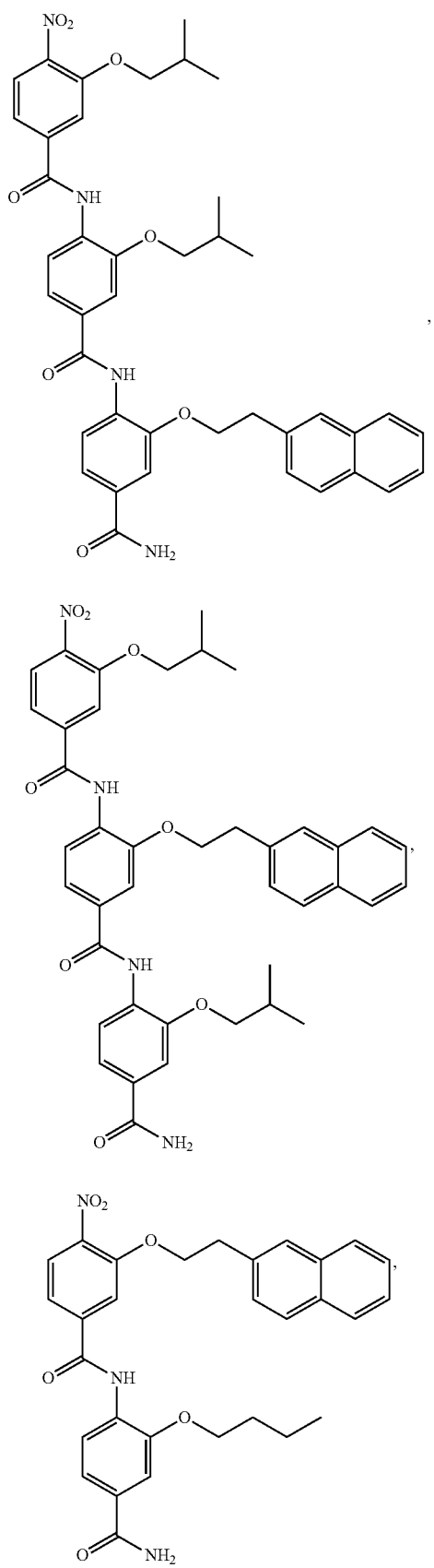
46
-continued
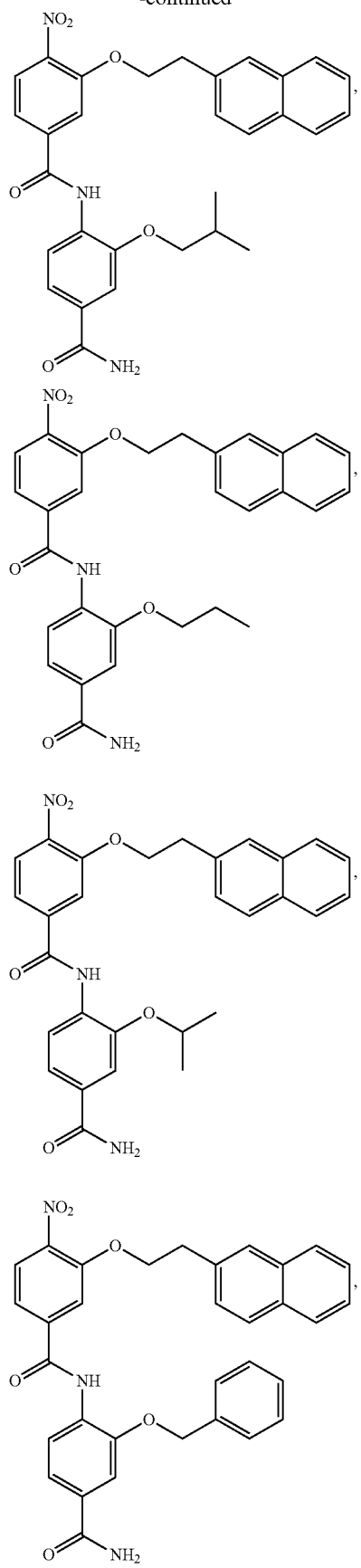

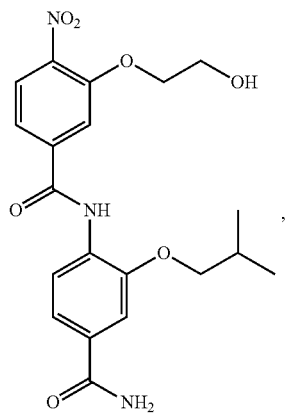
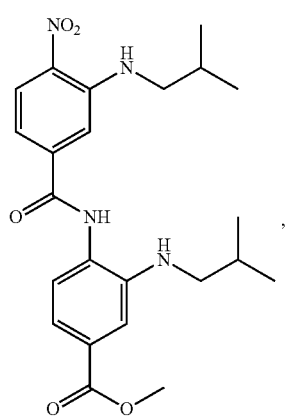
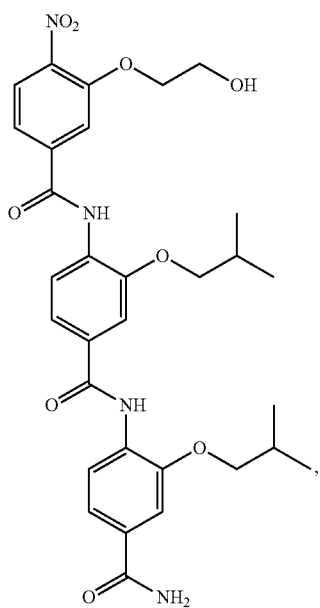
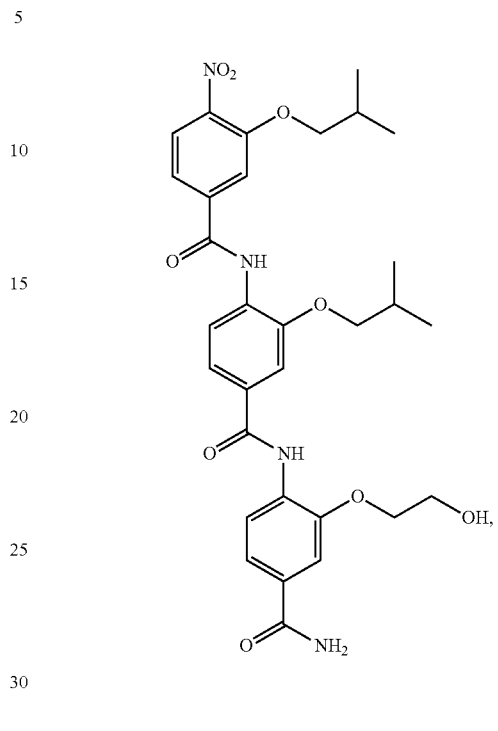
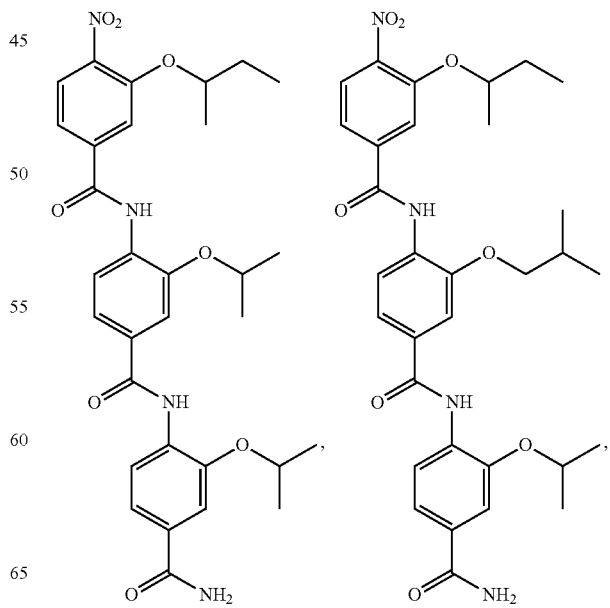

-continued

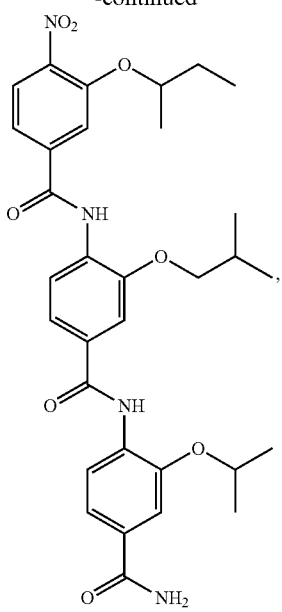

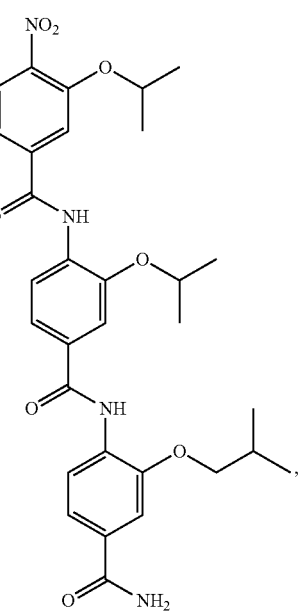

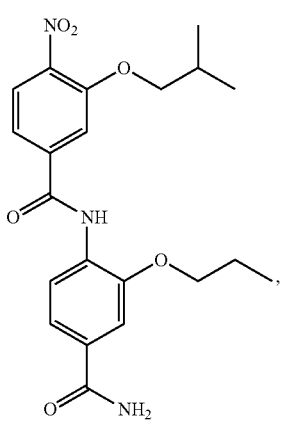

-continued

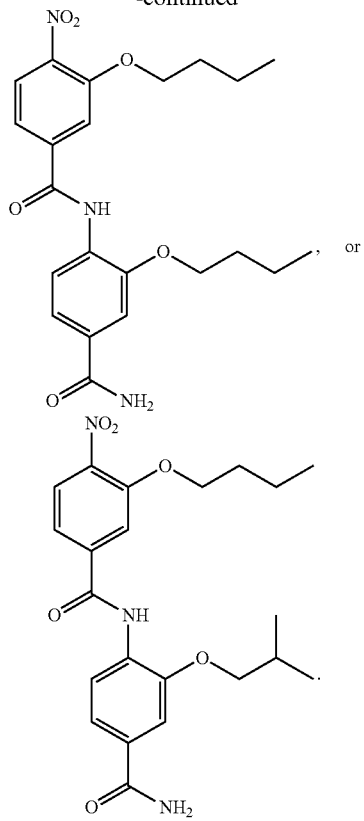

14. A method of inhibiting a prostate tumor cell in a subject comprising administering to said subject a therapeutically sufficient amount of an oligo-benzamide peptidomimetic compound as shown in claim 1.

15. The method of claim 14, wherein the prostate tumor cell is an androgen receptor (AR)- or estrogen receptor (ER)-positive tumor cell.

16. The method of claim 14, prostate tumor cell is a carcinoma cell.

17. The method of claim 14, wherein administering comprises local, regional, systemic, or continual administration.

18. The method of claim 14, wherein said peptidomimetic compound is fused to a cell delivery domain.

19. The method of claim 14, wherein inhibiting comprises inducing growth arrest of said prostate tumor cell, apoptosis of said prostate tumor cell and/or necrosis of a prostate tumor tissue comprising said prostate tumor cell.

20. The method of claim 14, further comprising providing to said subject a second anti-cancer therapy.

21. The method of claim 20, wherein said second anti-cancer therapy is surgery, chemotherapy, radiotherapy, hormonal therapy, toxin therapy, immunotherapy, and cryotherapy.

22. The method of claim 20, wherein said second anti-cancer therapy is provided prior to administering said compound.

23. The method of claim 20, wherein said second anti-cancer therapy is provided after administering said compound.

24. The method of claim 20, wherein said second anti-cancer therapy is provided at the same time as said compound.

25. The method of claim 14, wherein said subject is a human.

26. The method of claim 14, wherein said compound is administered at about 0.1 to about 100 mg/kg.

27. The method of claim 26, wherein said compound is administered at about 1 to about 50 mg/kg.

28. The method of claim 14, wherein said compound is administered daily.

29. The method of claim 14, further comprising assessing AR- or ER-driven gene expression in said prostate tumor cell of said subject after administering said compound.

30. A pharmaceutical composition comprising a compound as shown in claim 1, dispersed in a pharmaceutically acceptable carrier, buffer or diluent.

31. The method of claim 28, wherein said compound is administered daily for 7 days, 2 weeks, 3 weeks, 4 weeks, one month, 6 weeks, 8 weeks, two months, 12 weeks, or 3 months.

32. The method of claim 14, wherein said compound is administered weekly.

33. The method of claim 32, wherein said compound is administered weekly for 2 weeks, 3 weeks, 4 weeks, 6 weeks, 8 weeks, 10 weeks, or 12 weeks.

34. The method of claim 14, further comprising assessing AR- or ER-driven gene expression in said prostate tumor cell of said subject prior to administering said compound.

* * * * *

UNITED STATES PATENT AND TRADEMARK OFFICE
CERTIFICATE OF CORRECTION

PATENT NO. : 8,754,124 B2  
APPLICATION NO. : 13/683932  
DATED : June 17, 2014  
INVENTOR(S) : Jung-Mo Ahn and Ganesh Raj It is certified that error appears in the above-identified patent and that said Letters Patent is hereby corrected as shown below:

In the Claims

In claim 1, column 43, line 65, after "X is", insert -- $-NO_2$; and --.

In claim 13, column 47, lines 5-20, delete formula " 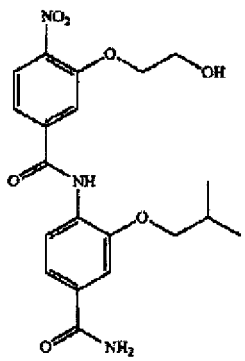 " and insert formula

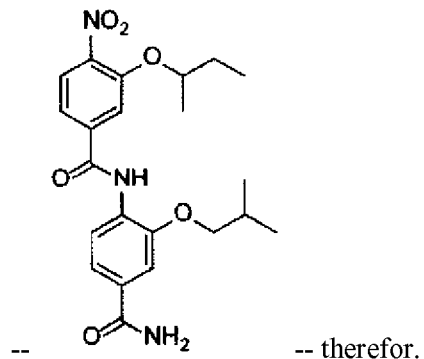 -- therefor.

Signed and Sealed this
Twenty-sixth Day of August, 2014

Michelle K. Lee
*Deputy Director of the United States Patent and Trademark Office*